United States Patent [19]

Heller et al.

[11] 4,249,531
[45] * Feb. 10, 1981

[54] BIOERODIBLE SYSTEM FOR DELIVERING DRUG MANUFACTURED FROM POLY(CARBOXYLIC ACID)

[75] Inventors: Jorge Heller, Palo Alto, Calif.; Richard W. Baker, Bend, Oreg.

[73] Assignee: Alza Corporation, Palo Alto, Calif.

[*] Notice: The portion of the term of this patent subsequent to May 21, 1991, has been disclaimed.

[21] Appl. No.: 54,788

[22] Filed: Jul. 5, 1979

Related U.S. Application Data

[60] Continuation of Ser. No. 750,701, Dec. 15, 1976, Pat. No. 4,180,064, which is a division of Ser. No. 591,443, Jun. 30, 1975, Pat. No. 4,014,987, which is a continuation-in-part of Ser. No. 467,246, Jun. 4, 1974, abandoned, which is a continuation-in-part of Ser. No. 318,831, Dec. 27, 1972, abandoned.

[51] Int. Cl.³ .............................................. A61M 7/00
[52] U.S. Cl. .................................. 128/260; 128/271; 424/33
[58] Field of Search ............................ 128/260, 271; 424/19–22, 33; 71/1, 65, 3, 64 F

[56] References Cited

U.S. PATENT DOCUMENTS

| | | | |
|---|---|---|---|
| 2,066,105 | 12/1936 | Hagedorn et al. | 424/33 |
| 2,897,121 | 7/1959 | Wagner | 424/33 |
| 3,080,346 | 3/1963 | Schellenberg et al. | 424/81 |
| 3,081,233 | 3/1963 | Enz | 424/33 |
| 3,143,472 | 8/1964 | Lappas et al. | 424/33 |
| 3,608,063 | 9/1971 | Banker | 424/33 |
| 3,811,444 | 5/1974 | Heller et al. | 128/260 |
| 3,888,975 | 6/1975 | Ramwell | 128/260 |
| 3,898,986 | 8/1975 | Zaffaroni | 128/260 |
| 3,914,402 | 10/1975 | Shell | 128/260 |
| 3,971,367 | 7/1976 | Zaffaroni | 128/260 |
| 3,986,510 | 10/1976 | Higuchi et al. | 128/260 |
| 4,014,987 | 3/1977 | Heller et al. | 128/260 |

FOREIGN PATENT DOCUMENTS 1124115  8/1968  United Kingdom ............... 128/260

OTHER PUBLICATIONS

Lappas, L. et al., *J. Pharm. Sci.*, vol. 56, pp. 1257–1261, 1967.
Heyd, A. et al., *J. Pharm. Sci.*, vol. 58, No. 5, pp. 586–588, 1969; vol. 59, No. 7, pp. 947–949, 1970.

*Primary Examiner*—Robert W. Michell
*Assistant Examiner*—C. F. Rosenbaum
*Attorney, Agent, or Firm*—Paul L. Sabatine; Thomas E. Ciotti; Edward L. Mandell

[57] ABSTRACT

A device for the controlled continuous administration of an active agent to an environment of use is disclosed. The device comprises a body of erodible agent release rate controlling material containing an agent dispersed therethrough; the rate controlling material is a hydrophobic poly(carboxylic acid) having one ionizable carboxylic hydrogen for each 8 to 12 carbon atoms, which material erodes at a controlled and continuous rate over a prolonged period of time in response to the environment by a process of carboxylic hydrogen ionization, thereby releasing the dispersed agent at a controlled rate over a prolonged period of time.

15 Claims, 9 Drawing Figures

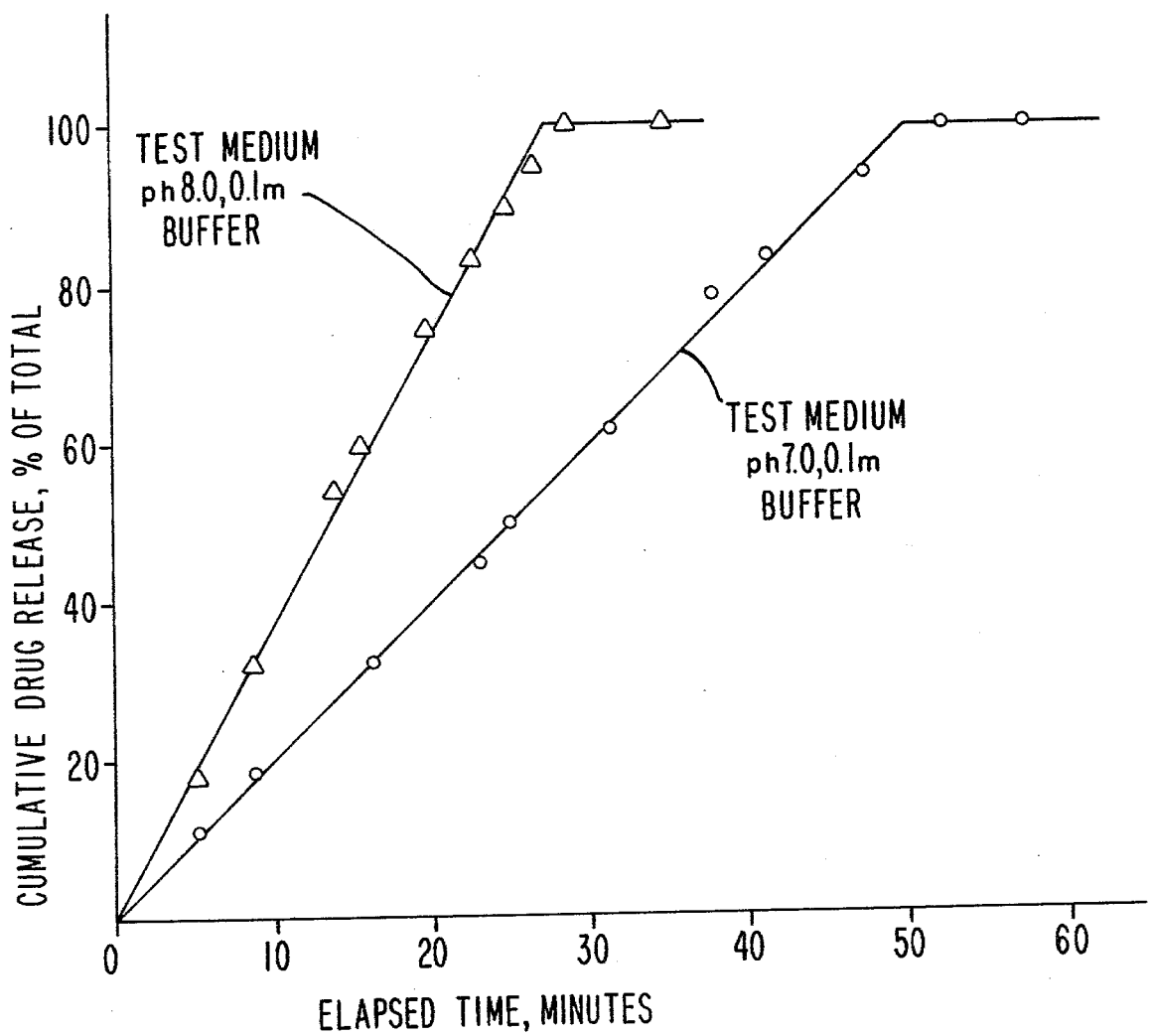

BIOERODIBLE SYSTEM FOR DELIVERING DRUG MANUFACTURED FROM POLY(CARBOXYLIC ACID)

CROSS-REFERENCE TO RELATED APPLICATIONS

This application is a continuation of United States Patent Application Ser. No. 750,701 filed on Dec. 15, 1976 and now U.S. Pat. No. 4,180,064 issued on Dec. 25, 1979, which application is a division of United States Patent Application Ser. No. 591,443 filed on June 30, 1975 and now U.S. Pat. No. 4,014,987 issued on Mar. 29, 1977, which division is a continuation-in-part of our copending United States Patent Application Ser. No. 467,246 filed on June 4, 1974, now abandoned, which latter application is a continuation-in-part of United States Patent Application Ser. No. 318,831 filed on Dec. 27, 1972 and now abandoned. This application and the earlier applications are assigned to the same assignee and benefit of their filing dates is claimed.

BACKGROUND OF THE INVENTION

1. Field of the Invention

This invention relates to device which dispense active agents to an environment of use at a controlled and continuous rate over a prolonged period of time. In a preferred embodiment, it relates to delivery devices for the sustained release of an agent to a substantially constant pH environment, such as an agent to a mammalian patient, and the like.

2. The Prior Art

The use of poly(carboxylic acids) as enteric coatings has been reported by Lappas and McKeehan at 51 *J. Pharm. Sci.* 808 (1962), at 54 *J. Pharm. Sci.* 176 (1965) and at 56 *J. Pharm. Sci.* 1257 (1967).

As is well known, enteric coatings are special coatings applied to ingestible tablets or capsules which prevent release and absorption of their contents until the tablets reach the intestines.

The poly(carboxylic acids) are well suited to this application and the widely varying pH conditions of the gastrointestinal tract. In the highly acidic stomach (pH 2) poly(carboxylic acids) are present completely as unionized hydrophobic species which are water insoluble and which prevent the release of any enclosed drug. As the poly(carboxylic acids) move on to the intestine, they are exposed to alkaline conditions (pH of up to 9) in which they ionize to soluble hydrophilic species and release the enclosed drug.

With these prior enteric coating teachings, the release of drug is merely delayed. The release is essentially a pH-dependent step function.

There is no release of drug in the acidic stomach; there is release of all the drug as the encapsulated drug enters the intestine and the pH of the environment changes to an alkaline value.

STATEMENT OF THE INVENTION

It has now been found that poly(carboxylic acids) may be used to form a device giving a controlled and continuous release of an active agent over a prolonged period of time under conditions of essentially constant pH. This is in direct contrast to the teachings of the prior art of the use of these materials in enteric coated pills which gave a step function release of drug under conditions of changing pH.

In accordance with this invention, a device is provided which permits the controlled and continuous administration of active agent to an essentially constant pH environment. Such a device comprises a body of erodible release rate controlling material containing the active agent dispersed therethrough. The release rate controlling material comprises a hydrophobic poly(carboxylic acid) having an average of one ionizable hydrogen for each 8 to 22 total carbon atoms. These polyacids erode in response to the environment of use at a controlled and continuous rate by a process of carboxylic hydrogen ionization. This erosion extends over a prolonged period of time and causes the dispersed agent to be released at a controlled and continuous rate over a prolonged period of time.

In a preferred embodiment, the invention involves a device for delivering drugs to a substantially constant pH environment within the body of a mammalian patient, with the device eroding when placed in the body in response to the environment.

Such a device comprises a body of the hydrophobic poly(carboxylic acid) having drug dispersed therethrough. When this device is placed in a substantially constant pH environment within the body of a mammalian patient, the poly(carboxylic acid) bioerodes by a process of carboxylic hydrogen ionization in response to the mammalian environment and gradually releases drug at a controlled and continuous rate over a prolonged period of time.

The invention further makes possible a process for the controlled and continuous administration of drugs to a mammalian patient over prolonged periods of time. This process involves employing the drugs in a certain form, and applying this form to an environment in the mammalian patient which is characterized as having an essentially constant pH throughout the period of administration of drug. The drug form employed in this process comprises a body of drug release rate controlling hydrophobic poly(carboxylic acid) having one ionizable carboxylic hydrogen atom for each 8 to 22 carbon atoms and having the drug dispersed throughout, that bioerodes in response to the environment.

In another embodiment, the invention provides devices for the local delivery of drug to the uterus and vagina which devices are of simple operation, give a reliable delivery of drug over a prolonged period of time, and bioerode in the uterus or vagina in response to the environment thereof.

The invention also provides devices for the local and systemic delivery of drug wherein the device is a nasal, anal, buccal, topical, implant, body passageway, or non-reproductive body cavity device for the controlled and continuous delivery of drug as the device erodes in response to the environment wherein the device is placed for release of drug thereto.

The invention also provides for devices for the release of an active agent to a non-biological environment with the device releasing active agent at a controlled and continuous rate as the device erodes in response to the environment.

BRIEF DESCRIPTION OF THE DRAWINGS

In the drawings:

FIG. 3 is a perspective view of a disc-shaped tablet suitable for releasing drugs perorally or subcutaneously or for releasing other active agents to other constant pH environments.

FIG. 4 illustrates in perspective a device of this invention adapted to release a controlled amount of active agent into a liquid medium.

FIG. 5 is a cross-sectional view of a suppository embodying the present invention.

FIG. 6 is a partially cut away elevational view of an intrauterine device formed of two connecting rings.

FIG. 7 is a partially cut away elevational view of an intrauterine device shaped like a "T", adapted to release a controlled amount of active agent into the uterus.

FIG. 9 is a graph illustrating the linear release of active agent achieved with devices of this invention.

DETAILED DESCRIPTION OF THE INVENTION

In accord with this invention, agents may be most advantageously delivered to the environment of use over a prolonged period of time by being incorporated in a body of hydrophobic poly(carboxylic acid) of from 8 to 22 carbons per ionizable hydrogen. This body slowly erodes in the environment of use and is incorporated in a device adapted and sized for insertion, positioning and placement in the environment of use throughout the period of agent administration.

The terms "hydrophobic" and "hydrophobicity" broadly refer to the property of a substance to not absorb or adsorb appreciable amounts of water. As used in this specification and claims, a more precise meaning of these terms is intended; a hydrophobic material is defined as one which absorbs or adsorbs water in a maximum amount not exceeding 10% of its dry weight.

The phrase "active agent" and the term "agents" as used in this specification and accompanying claims comprise any compound, or mixture of compounds, composition of matter or mixture thereof which when dispensed produces a beneficial result for man, animals or the environment of use.

As used herein, the phrase "a prolonged period of time" shall have different meanings with respect to the various delivery devices and the environment of use to which it is applied. Normally, it will mean a time period of at least ½ hour to 180 days, and it includes one hour of higher, up to two years or more.

In accordance with the present invention, there is provided a device for the conrolled continuous dispensing of a predetermined amount of active agent over a prolonged period of time.

Figure 1:
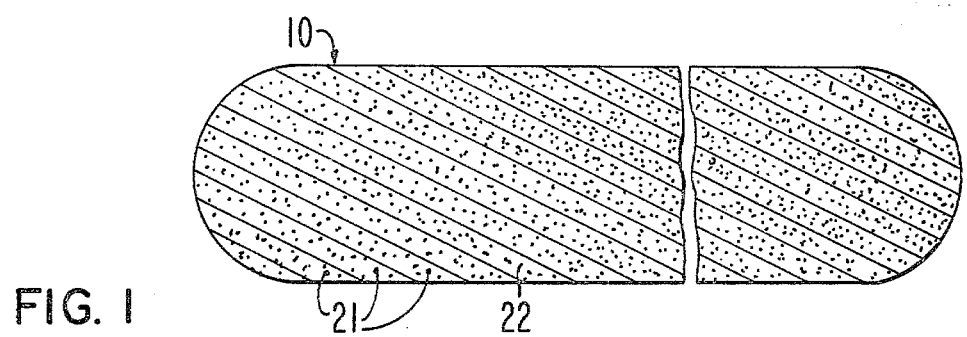
FIG. 1 is a cross sectional view of a device in accord with this invention for releasing active agent at a controlled rate over a prolonged period of time.

Such a device is shown as device 10 in FIG. 1. In FIG. 1, device 10 comprises an active agent 21 dispersed throughout a body 22 of hydrophobic poly(carboxylic acid). When placed in an environment having a controlled and essentially constant pH, poly(carboxylic acid) body 22 bioerodes concommitantly releasing the active agent which is dispersed therethrough.

The polyacids employed are characterized as being hydrophobic when unionized and as having a specified proportion of carboxylic hydrogens. They are substantially impermeable to the passage of agent and biological fluids and release entrapped agent by an erosion control process, since these poly(acids) gradually erode in the environment; preferably a biological environment, at a controlled rate by a process of carboxylic hydrogen ionization. These poly(acids) and their erosion products are nontoxic and non-irritation to biological tissues such as the endometrium and other uterine and vaginal tissues.

Suitable poly(carboxylic acids) are the hydrophobic poly(acids) which are represented by the general formula:

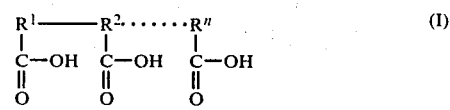

wherein: the R's are organic radicals independently selected to provide, on average, from 8 to 22 total carbon atoms for each carboxylic hydrogen. Variations of this ratio within this range can vary the erosion and active agent release rates to devices prepared from these polymeric acids. Organic radicals represented by $R^1, R^2, \ldots R^n$ may be selected from hydrocarbon radicals and hetero-atom containing organic radicals. Suitable hetero atoms for employment in $R^1, R^2, \ldots R^n$ include oxygen, nitrogen, sulfur, and phosphorous as well as other hetero atoms so long as the required hydrophobicity and carbon to carboxylic hydrogen average ratio is maintained. The value of n and hence the average molecular weight of the polymer is not critical and may vary over a wide range. Suitable molecular weights, for example, range from about 10,000 to about 800,000. Materials within this range erode to products which may be easily and innocuously passed from the environment of use. Preferred molecular weights are from about 15,000 to about 500,000.

While not wishing to limit the scope of the poly(acids) intended to be employed in accord with this invention, and while alternative materials and preparative schemes are set forth in the description of suitable poly(acids) which follows, practically speaking, the most common and widely applied method for introducing a carboxylic acid function, as well as other hetero atom functions, into a polymeric material of the type employed in this invention, is to proceed through monomers having a carbon skeleton of at least two carbon atoms. These monomers contain polymerizable olefinic carbon-carbon double bonds. At least a portion of these monomers will have appended thereto one or more carboxyl radicals, or suitable precursors thereof and optionally also other hetero atom radicals. The polymer is formed by effecting addition of these monomers, one to another, across the polymerizable double bonds. This general method for forming poly(acids) is well known and does not comprise a part of the present invention. This preparative method may be generally represented by the reaction:

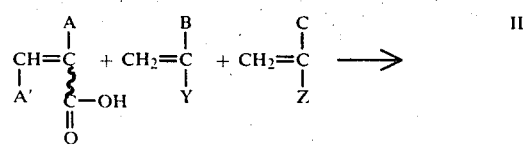

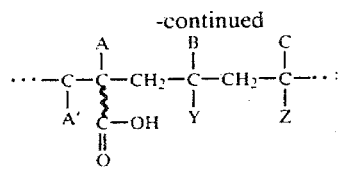

wherein A represents hydrogen or a hydrocarbon and

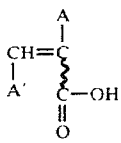

represents a carboxyl group (or carboxy group precursor) containing monomer also containing a polymerizable olefinic double bond. Such monomers include, for example, acrylic acid, substituted acrylic acid, maleic acid, maleic anhydride, crotonic acid and the like.

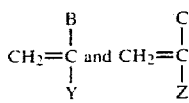

represent organic monomers containing a polymerizable double bond which may be the same or different than

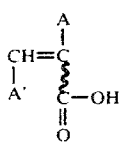

This preparative technique can be employed to prepare poly(carboxylic acids) in accord with General Formula I having hydrocarbon R's either by polymerizing suitable hydrocarbon substituted olefinically unsaturated acids such as substituted acrylic acids and crotonic acids or by copolymerizing olefinically unsaturated acids, such as acrylic acid or hydrocarbon-substituted acrylic acids or the crotonic acids, with unsaturated hydrocarbons. Suitable poly(carboxylic acids) having hydrocarbon R's prepared by polymerizing substituted acrylic acids may be represented by the general formula:

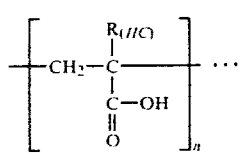
(III)

wherein $R_{(HC)}$ represents hydrocarbon substitutes averaging from 5 to 15 carbon atoms in size, for example n-pentyl, cyclohexyl, pehnyl, n-decyl, 2,2-diethyldecyl, combinations of butyl and hexyl, and the like. Such materials may be prepared by polymerizing the corresponding hydrocarbon substituted acrylic acid monomers with free radical initiators as described in U.S. Pat. No. 2,904,541 issued Sept. 15, 1959.

Also useful are poly(carboxylic acids) prepared by copolymerizing unsaturated carboxylic acids as acrylic acid (or substituted acrylic acid) with a polymerizable hydrocarbon. These acids may be represented by the general formula:

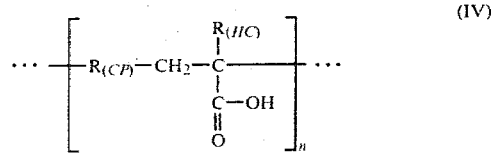
(IV)

wherein $R_{(HC)}$ is a hydrocarbon radical of up to about 12 carbons or hydrogen; and $R_{(CP)}$ is a copolymerized hydrocarbon group. The hydrocarbons which may be copolymerized with unsaturated carboxylic acids include terminally olefinically unsaturated hydrocarbons and olefinically unsaturated hydrocarbons having a conjugated carbon-carbon double bond. Thus, typical hydrocarbon groups represented by $R_{(CP)}$ include ethyl, propyl, butyl, isopentyl, and phenylethyl as result when ethylene, propylene, butadiene, isoprene and styrene, respectively, are copolymerized with unsaturated acids. Such preparations are set forth in 10 *J. Poly. Sci.* 441 (1946 Series) and 10 *J. Poly. Sci.* 597 (1946 Series).

Poly(carboxylic acids) in accord with General Formula I having hydrocarbon R's may also be prepared by other known techniques, such as for example by oxidizing terminal methyl groups on suitable hydrocarbon polymers to carboxyl groups with alkaline permanate as described in Cram and Hammond *Organic Chemistry*, 2nd Ed., pages 525-6; or by carboxylating olefinically unsaturated hydrocarbon polymers by contacting them with carbon monoxide, water and optionally some hydrogen under conditions of elevated temperature and pressure in the presence of stongly acidic catalysts, for example HF, $BF_3$, $H_2SO_4$ and the like.

Poly(carboxylic acids) useful in the devices of the invention and illustrated by General Formula I may suitably incorporate oxygen atoms in their R's. Oxyhydrocarbon R's include ester groups or ether groups. Poly(carboxylic acids) represented by Formula I incorporating ester groups, as R's, are especially suitable in devices of this invention. They may be readily prepared by partially esterifying acid polymers or copolymers, which are themselves easily obtained. They offer the advantage of permitting simple variation of the ratio of carbons to ionizable carboxylic hydrogens by varying the extent of partial esterification or the esterifying alcohol employed. As a result, easy adjustment of erosion characteristics of the poly(carboxylic acid) product and hence active agent release rate, is obtained.

As an example of this easy control, consider the case of poly(carboxylic acid). Poly(acrylic acid) is available commercially or may be easily prepared such as by mixing 167 parts of 60% acrylic acid, 232 parts of water, 0.50 parts of potassium peroxydisulfate and 0.25 parts of potassium metabisulfite and heating the mixture to 60° C. Poly(acrylic acid) per se, however, is not a suitable poly(carboxylic acid) for use in devices of this invention as it is substantially hydrophilic and water soluble and does not have the carbon to ionizable hydrogen ratio necessary to give suitable erosion and active agent release characteristics.

When half the carboxyl groups of poly(acrylic acid) are esterified by reaction with an alkanol such as hexanol, the resulting partial ester is hydrophobic and has a carbon to ionizable hydrogen ratio within the range necessary for materials employed in the devices of this invention (i.e., 12:1). A similarly suitable material would result if ⅔ of the poly(acrylic acid) carboxyl groups were esterified with ethanol.

This partial esterification technique is of course not limited to treatment of acrylic acids. Any organic lower poly(carboxylic acid) may be partially esterified when necessary to achieve the required hydrophobicity and carbon to acidic hydrogen ratio. Other poly(acids) which often benefit from esterification include homopolymers of unsaturated lower carboxylic acids such as the lower alkyl acrylic acids, for example methacrylic and ethacrylic acid; crotonic and propiolic acid; maleic acid and fumaric acid. Polymers of acid precursors such as poly(maleic anhydride) may be hydrolyzed and partially esterified as well. Also suitable for esterification are acids or precursors copolymerized with lower unsaturated hydrocarbons of from 2 to 8 carbons such as ethylene, propylene, butadiene, styrene and the like, or with lower unsaturated oxyhydrocarbons such as unsaturated ethers of from 3 to 8 carbon atoms. Many of these polymers and copolymers are available commercially. Others can be prepared by bulk, solution, emulsion or suspension polymerization using free radical initiators at 40°–100° C., all methods well known in the art. The partial esterification may be conveniently effected by contacting the acid-containing polymers with a controlled quantity of the esterifying alcohol at elevated temperature, optionally in the presence of an acidic esterification catalyst. Alcohols suitable for partially esterifying the above-noted poly(acids) include the hydrocarbon alcohols, preferably the alkanols of from about one to about 16 carbon atoms; for example, methanol, ethanol, isopropanol, n-butanol, cyclohexanol, octanol, the decanols, and n-dodecanol. Combinations of alcohols may also be employed.

In addition to being included in partially esterified poly(carboxylic acids), as noted above, ether linkages may be included generally in the polymers employed in this invention; that is, they may be oxyhydrocarbon R's in General Formula I. Ether groups may be incorporated by copolymerizing an unsaturated carboxylic acid with an unsaturated ether, for example, acrylic acid, maleic acid, crontonic acid and the like with the vinyl ethers of from about 3 to about 10 carbon atoms such as methyl vinyl ether, ethyl vinyl ether, butyl vinyl ether, hexyl vinyl ether, and the like; for example, by the method described in U.S. Pat. No. 2,927,911. Because of the small number of carbon atoms in many of these unsaturated ethers and acids, it may be desirable, to achieve the required carbon/acid hydrogen ratio, to terpolymerize these materials with a non-carboxylic hydrogen-containing material, most suitably an unsaturated terpolymerizable unsaturated hydrocarbon of from 2 to 8 carbon atoms such as ethylene, butadiene, or styrene. Examples of terpolymers are presented hereinafter.

The R's of General Formula I, as oxyhydrocarbons, may contain alcohol linkages. The employment of alcohol linkage-containing oxyhydrocarbons as R's can pose a problem, however, as the alcohol linkages generally decrease the hydrophobicity of the poly(acid), often to below the extent of hydrophobicity required of poly(acids) for employment in this invention. It is usually possible to incorporate up to about 10%, basis total polymer, of alcohol linkage-containing R's in the poly(acids).

Nitrogen, sulfur and phosphorous atoms may also be incorporated in R groups employed in the polymers represented by General Formula I. Nitrogen may be present as cyano groups, amide groups or imide groups. Amine groups are generally not suitable as they can result in internal salts being formed between the polymerized acid and amine groups. Sulfur atoms may be present as mercaptan or disulfide linkage, while phosphorous atoms may be present as phosphate linkages.

A preferred group of materials from which to fabricate the dispensing devices of this invention comprise hydrophobic polymers of an acid selected from acrylic acid, lower alkyl acrylic acids of from 4 to 6 carbon atoms per monomeric unit, and maleic acid; either alone or copolymerized with up to about 2 moles, per mole of acid of a copolymerizable olefinically unsaturated group such as ethylene or lower (1 to 4 carbon) alkyl vinyl ethers wherein from about 20% to 90% of the acid groups have been esterified with an alkanol of from 1 to about 10 carbon atoms and wherein the ratio of total carbon atoms to acidic carboxylic hydrogens is in the range of from about about 9:1 to about 20:1.

An even more preferred group of poly(carboxylic acids) comprise the hydrophobic partially esterified copolymers of acrylic acid, methacrylic acid or maleic acid with from 0.2 to 1.5 moles, per mole of acid of ethylene or lower (1–4 carbon) alkyl vinyl ether having from about 35% to about 70% of their total carboxylic groups esterified with lower alkanol of from about 3 to about 10 carbon atoms, said copolymers having a carbon to acidic carboxylic hydrogen ratio of from about 10:1 to about 15:1.

A group of poly(carboxylic acids) most preferred for use in accord with the present invention comprise hydrophobic copolymers of maleic acid with about one mole, per mole of maleic acid, of ethylene or methyl vinyl ether, said copolymer having about half of its total carboxylic groups esterified with a lower monoalkanol of from 4 to 8 carbon atoms, wherein the carbon to acidic carboxylic hydrogen ratio has a value of from about 10:1 to about 14:1.

A presently preferred group of poly(carboxylic acids) are terpolymers of at least one $\alpha,\beta$-unsaturated aliphatic acid of 3 to 8 carbons, an alkyl ester of such $\alpha,\beta$-unsaturated aliphatic acids in which said alkyl is of 2 to 8 carbon atoms. Typical terpolymers include one acid monomer and two ester monomers, two acid monomers and an ester monomer of the acid functionality, an acid monomer, an ester monomer of the acid functionality and an acid monomer having a lower alkyl group, and the like. A particularly preferred terpolymer is comprised of 60 to 75 mol % of a lower alkyl acrylate of the formula $CH_2=CH-COOR_9$ where $R_9$ is an alkyl of 2 to 8 carbons, from 15 to 30 mol % of an acid of the formula $CH_2=CR_{10}-COOH$ where $R_{10}$ is an alkyl of 1 to 8 carbons, and from 5 to 15 mol % of an acid of the formula $CH_2=CHCOOH$, and the like. A terpolymer included in this preferred group is comprised of 60 to 75 mol % butyl acrylate, 15 to 30 mol % methacrylic acid and 5 to 15 mol % acrylic acid. The terpolymers have a molecular weight range of 10,000 to 1,000,000 or higher.

Typical carboxylic acid monomers useful for producing the terpolymer are the olefinically unsaturated carboxylic acid containing at least one activated carbon-to-carbon olefinic double bond, and at least one carboxyl group, that is, an acid containing an olefinic double bond which functions in polymerization because of its presence in the monomer molecule either in the alpha-beta position with respect to the carboxyl group, such as

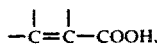

or as a part of a terminal methylene grouping $CH_2=C<$. Olefinically unsaturated acids of this broad class include acrylic acids such as acrylic acid itself, methacrylic acid, ethacrylic acid, crotonic acid, sorbic acid, cinnamic acid, beta-styryl acrylic acid, hydromuconic acid, itaconic acid, citraconic acid, and the like. As used for the terpolymer herein, the term carboxylic acid includes poly(carboxylic acids) and those acid anhydrides, such as maleic anhydride, wherein the anhydride group is formed by the elimination of one molecule of water from two carboxyl groups located on the same poly(carboxylic acid) molecule. The anhydrides have the general formula

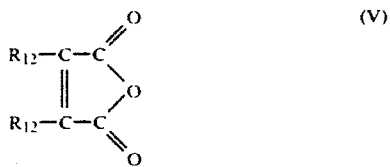

(V)

wherein $R_{12}$ are selected from the group consisting of hydrogen, halogen, cyanogen, hydroxyl, lactam, alkyl and the like. The term alkyl as used herein includes the straight and branched chain alkyl groups such as methyl, ethyl, propyl, isopropyl, butyl, pentyl, hexyl, 2-methyhexyl, heptyl, and the like.

Representative esters suitable for synthesizing the terpolymer include without limitation methyl methacrylate, ethyl methacrylate, n-butyl methacrylate, isobutyl methacrylate, t-butyl methacrylate, hexyl methacrylate, lauryl methacrylate, and other acrylates such as cyclohexyl methacrylate, dimethylaminomethacrylate, 2-hydroxymethylmethacrylate, and the like. Acrylic esters of the formula $CH_2=CHCOOR$ includes the n-alkyl esters methyl, ethyl, propyl, butyl, pentyl, hexyl and heptyl, the secondary and branched chain alkyl esters isopropyl, isobutyl, sec-butyl, 2-methylbutyl, 3-methylbutyl, 1-ethylpropyl, 1-methylhexyl and the like. Acrylic acid, its esters and other derivatives are commercially available and known to the art in *Encyclopedia of Chemical Technology*, Kirk-othmer, Vol. 1, pages 285 to 313, 1963; *Encyclopedia of Polymer Science and Technology*, Vol. 1 pages 197 to 226 and 246 to 328, 1964, in U.S. Pat. No. 3,137,660, and the like.

The poly(carboxylic acids) employed in the device of this invention are soluble in organic solvents. Accordingly, the poly(acids) may be conveniently formed by film casting techniques. An organic solvented solution of the poly(acid), optionally containing active agent, is prepared and cast or drawn to a flim. The solvent is then evaporated to yield a continuous film of the poly(acid). The devices may them be punched or cut from this film. Alternatively, the devices may be molded from such a solution.

A wide range of organic solvents may be used for the casting solutions. With poly(carboxylic acid) materials having total carbon to carboxylic hydrogen ratios at the lower end of the range specified for this invention, such as ratios in the range of from about 8:1 to about 11:1, it is generally preferred to use relatively polar organic solvents, that is, organic solvents having dielectric constants, as listed in the 51st Edition of the Chemical Rubber Company "Handbook of Chemistry and Physics" at pages E-62 through E-64, of greater than about 15, for example, lwoer alkanols such as methanol, ethanol, the propanols, 1- and 2-butanol, lwoer alkanones such as acetone, diethyl ketone, ethyl methyl ketone and cyclohexanone and halogenated and nitrogenated solvents such as 2-chloroethanol, and nitrobenzene. With poly(carboxylic acids) having higher ratio of total carbon atoms to ionizable hydrogens, such as from about 14:1 to 22:1, it is generally preferred to use less polar organic solvents, such as those having dielectric constants of less than about 15, especially less than about 10, for example, ethers such as diethyl ether, isopropyl ether and the like, hydrocarbons such as cyclohexane, benzene and toluene, and other low dielectric materials such as ethyl acetate. With the intermediate ratio poly(carboxylic acids) either group of solvents may be used with the alkanols and alkenones generally being favored.

The casting and drying are carried out at moderate conditions such as at ambient temperature and pressure. Solvent removal may be facilitated by the use of vacuum or slightly elevated temperatures. However, substantially elevated temperatures, such as about 100° C., for lengthy periods, such as for several hours, may be deleterious to some agents or poly(carboxylic acids).

It is often desired to incorporate plasticizers in the poly(carboxylic acid) materials to improve or vary their physical properties, such as to make them more flexible. Exemplary plasticizers suitable for employment for the present purpsoe are the pharmaceutically acceptable plasticizers conventionally used, such as acetyl tri-n-butyl citrate, epoxidized soy bean oil, glycerol monoacetate, polyethylene glycol, propylene glycol dilaurate, decanol, dodecanol, 2-ethyl hexanol, 2,2-butoxyethoxyethanol and the like. The proportion of optional plasticizer used will vary within broad limits depending upon the characteristics of the poly(carboxylic acid) involved. In general, from about 0.01 parts to about 0.2 parts by weight of plasticizer for each part by weight of the poly(carboxylic acid) can be used. When plasticizers are included in the poly(carboxylic acid) materials they are most suitably added prior to shaping the final formed structure, such as by dissolving or dispersing them in the solution from which the form is cast.

Active agent is released from the delivery devices of this invention by erosion of the poly(carboxylic acid) body through which the agent is dispersed. As the body erodes, it releases the dispersed, entrapped agent. The poly(carboxylic acids) from which the bodies of the device of this invention are formed, are substantially imperforate and impermeable to the passage of active agent by diffusion. Hence, the rate of agent release is proportional to the rate of poly(carboxylic acid) erosion. When the rate of erosion is constant, the rate of release of agent will also be constant, assuming that the dispersion of agent through the body is uniform and that the area of the device which is eroding remains constant.

The aforementioned poly(carboxylic acid) erodes at a controlled rate when placed in an environment having a substantially constant pH. Environments in which the present devices give very suitable controlled rates of erosion comprise aqueous environments having a pH throughout the period of use of the device selected in the range of from about 6.0 to about 9.0. To give a smooth erosion and hence smooth release of agent, the pH should not vary by more than about ±0.5 pH units over the life of the device. Preferred environments vary by not more than about ±0.4 pH units and have a median pH in the range of from about 6.5 to about 8.5. The more alkaline the pH the more rapidly a given poly(carboxylic acid) erodes and releases entrapped agent. At pH's more than about 6.0, the rate of erosion is too slow to be practical, while at pH's more basic than about 9.0, the rate is uncontrollably fast.

Devices of this invention are useful for delivering all types of active agents to all sorts of aqueous environments which have the required pH characteristics. They find excellent and preferred application in drug delivery devices. In such applications, they delivery drugs to those environments within a mammalian patient which exhibit a constant pH in the range of from about pH 6.0 to about pH 9.0 throughout the period of use. Unlike the gastrointestinal tract which presents a variably acidic and basic pH environment, many areas of mammalian bodies have essentially constant pH's which fall within the desired pH 6–pH 9 range. For example, the rectum has a pH of about 7.5. The pH of blood is normally constant at about 7.2. In one of the presently preferred embodiments, the aforementioned device uterine erodes at uterine pH of 7 to 7.6, usually 7.2 to 7.3 in the substantially constant pH of the uterus. The products of erosion are innocuous to uterine endometrium and surrounding tissues. When a device in accord with this invention carrying drug is applied to any of these body areas, or similar body areas, it erodes at a controlled and constant rate over a prolonged period of time. The products of this erosion of the device are innocuously passed from the body. To increase compatibility with the body, it may be desirable to coat the devices of this invention with a non-interfering material such as a hydrophilic polymer, for example polyvinyl alcohol, gelatin, or the like.

DETAILED DESCRIPTION OF THE DRAWINGS

FIG. 1, as already noted, illustrates generically the delivery device 10 of this invention. Device 10 comprises drug 21 dispersed through poly(acid) body or matrix 22. Drug 21 may assume a variety of configurations in device 10. It may be in the form of liquid or solid particles, droplets, a colloid, a molecular solution or other form which is dispersed through body 22. Device 10 is shown sectioned. In the embodiment shown, device 10 is longer than it is wide and thickness is its shortest dimension. Device 10 also can be wider than it is long, or in another embodiment, device 10 is substantially longer than it is thick. A preferred pattern of erosion and release results when the thickness of the device is smaller than either of its other dimensions, preferably the thickness is less than 10% of the length or width. With such a configuration, an essentially constant surface area is presented throughout the period of erosion. Since erosion rate and hence agent release rate, are proportional to surface area, a constant, or zero order, rate of release results. Exemplary shapes of such "zero order release devices" would be an 8 mm disc and a 6 mm by 12 mm ellipsoid, each punched out of 0.4 mm thick drug-containing poly(carboxylic acid) sheet. The mechanism by which active agent is released by the poly(carboxylic acid) bodied devices of this invention offers distinct advantages.

In general, when a body of erodible material having active agent dispersed therethrough is placed in an aqueous environment, the following release mechanisms can occur depending upon the nature of the erodible material: If the erodible enclosing material is hydrophilic, it will absorb aqueous liquid and swell. Agent can then diffuse out through channels of absorbed fluids at rates which are often uneven, unpredictable, difficult to control and highly dependent upon the solubility of the agent in the fluid. If the agent is soluble in the fluids to an extent greater than about 50 parts per million weight, release is rapid and substantially uncontrolled. If the erodible enclosing material is hydrophobic but porous, it gives similar diffusion-controlled rates, with the same problems. If the enclosing material is hydrophobic and non-porous, as are the certain poly(carboxylic acids) employed in the present invention, the rate of agent release is controlled by the rate at which the enclosing material (matrix 21 in FIG. 1) is eroded or solubilized and enclosed agent (22 in FIG. 1) is uncovered. Such a mechanism offers the advantages of being more easily controlled and of providing a more uniform rate of drug release.

The poly(carboxylic acids) employed in the devices of this invention have proven especially advantageous for erosion-controlled release of drugs to the body. Without intent to limit the scope of this invention by theoretical considerations, it is believed that the uniform and controllable rates of erosion observed with devices comprising hydrophobic poly(carboxylic acids) having an average of 8 to 22 carbons for each ionizable acidic-carboxylic hydrogen are the result of equilibriums inherent in the erosion of these poly(carboxylic acids).

As shown in General Formula I, the poly(carboxylic acids) of this invention may be represented as:

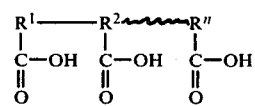

The carboxyl groups are weak acids which, in their unionized form, are hydrophobic. When placed in an aqueous fluid, a portion of the carboxyl groups ionize to yield hydrophilic

groups and hydronium ions ($H_3O^+$). As more of the carboxyl groups in an initially hydrophobic polymer chain ionize, the chain assumes an increasingly hydrophilic character and eventually goes into solution in the fluid. This solubilization by ionization occurs only on the outer surfaces of the poly(carboxylic acid) bodies. Even if minor amounts of fluid do penetrate the surface of the bodies, insignificant ionization can occur there since the inner carboxyl groups, being surrounded by an essentially organic medium exhibit a far higher pKa than do the carboxyl groups on the surface, which are in a more aqueous medium.

The bioerosion by surface ionization is a reversible reaction, the equilibrium of which is highly sensitive to pH, and thus, often self-limiting. As hydronium ions are generated, they tend to cluster about the polymer body from which they were generated, lower the pH in the area of the body, and prevent further solubilization by ionization. Some of the clustered hydronium ions gradually disperse or are consumed by alkalinity of the fluid and are replenished via further ionization. The overall erosion rate which results with the poly(carboxylic acids) of this invention is surprisingly slow, perfectly suited for employment in erodible devices such as device 10 designed to release agents over prolonged periods such as periods of from about 1-2 hours to about 60 days. To operate effectively, there must be some removal of hydronium ions, such as the addition of fresh fluid or of base or by means of a buffer.

The self-limiting pH control inherent with these certain poly(carboxylic acids) offers the further advantage of preventing the pH of the fluid of use from dropping, by reason of excess hydronium ion release, to a level which would be irritating or corrosive.

The exact rate of erosion is in part dependent upon the chemical makeup of the poly(carboxylic acid). The more hydrophobic the poly(acid) is, the greater the number of ionized carboxyl groups necessary to solubilize it and the slower its erosion rate. Thus, by changing the hydrophobicity of the certain poly(acids), as may be done by varying their ratio of total carbons to ionizable hydrogens within the range in accord with this invention, the rate of erosion may be controlled.

Figure 2:
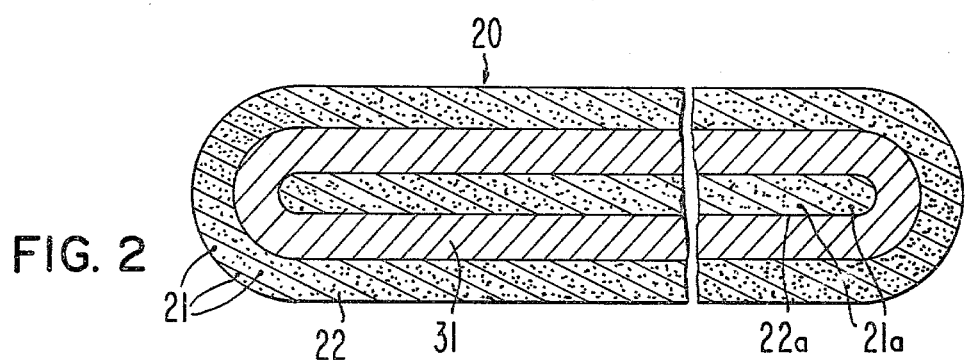
FIG. 2 is a cross sectional view of a multi-layered device in accord with the invention which releases active agent at a varying rate.

FIG. 2 illustrates, by reference numeral 20, an embodiment of this invention with which a variable rate of agent release may be achieved. Device 20 is comprised of a series of three concentric layers. The outer layer comprises a matrix 22 of ionizable hydrophobic poly(carboxylic acid) of this invention that can release agent 21 at a controlled rate over a prolonged period, in the same manner that the matrix in device 10 released agent. When the outer layer comprising matrix 22 and agent 21 has eroded away, middle layer 31 is exposed, and begins to erode. Layer 31 is formed from a bioerodible material, very suitably either the same or different hydrophobic poly(carboxylic acid) employed in matrix 22. Layer 31, as illustrated contains no agent, and thus during the erosion provides a period where no drug would be released. When layer 31 has been eroded, the innermost layer is exposed comprising ionizable hydrophobic poly(carboxylic acid) matrix 22a that has particles of agent 21a dispersed therethrough. As matrix 22a erodes, agent 21a is released at a controlled rate for a prolonged period of time. Many variations of device 20 will be apparent. For example, a greater number of layers may be employed, a variety of agents or concentrations may be employed in the several layers, or poly(acids) having different erosion rates may be used in different layers.

Figure 3:
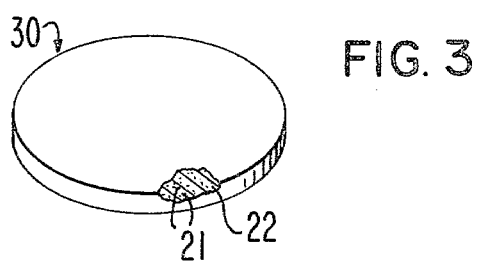
FIGS. 3-7 inclusive are illustrative of the many embodiments the present invention may take.

FIG. 3 illustrates in cut-away perspective view, by reference, numeral 30, a disc-shaped device in accord with this invention. Device 30 comprises particles of agent (drug) 21, dispersed throughout body 22 of poly(carboxylic acid). As body 22 erodes, agent 21 is released.

A device of such shape could find application as an agricultural additive for slowly releasing a variety of active agents such as biocides, fertilizers and the like to constant pH irrigation fluids. A device of such shape might also find application as a depot for drugs. For example, it could be placed in the sac of the eye, thereto release ocular drugs at a controlled rate for a prolonged period of time.

Figure 4:
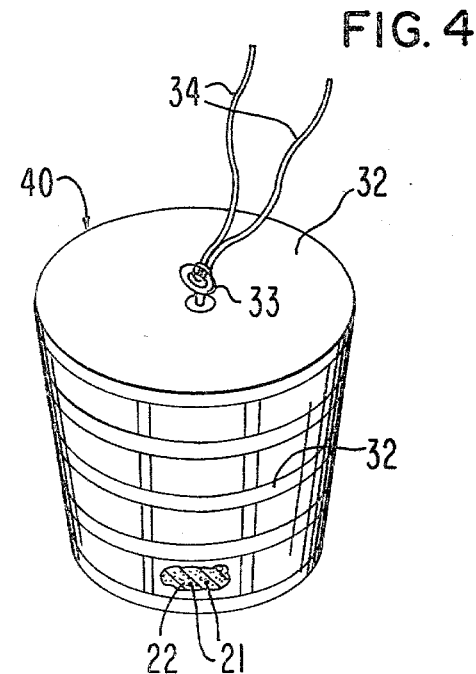

FIG. 4 illustrates in cut-away perspective view by reference numeral 40 an embodiment of this invention suitable for releasing an active agent to an aqueous environment of constant pH. Device 40 comprises active agent 21 dispersed through body 22 of poly(carboxylic acid). Said material is enclosed within net container 32 having ring 33 on its top surface and leads 34 attached to ring 33. Device 40 could be placed, for example, in a water closet and there attached by means of leads, where it would release detergent, disinfectant or the like to the water contained therein. Device 40 might also be affixed in a dishwasher or clothes washer where it would meter, as active agent, wash aids, water softeners, spot preventers, fabric softeners or the like to the wash water. Similarly, device 40 containing as active agent corrosion inhibitors or lubricants might be placed in an automobile cooling system where it would dispense such agents over a prolonged period of time.

Figure 5:
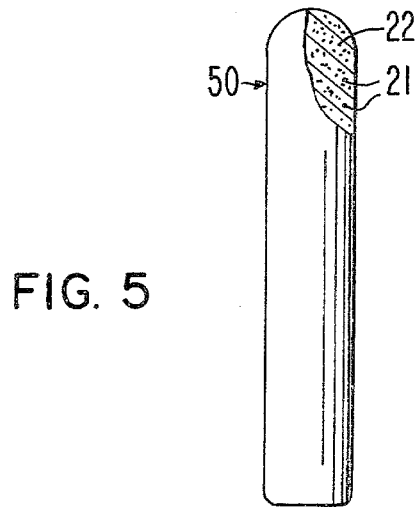
Figure 6:
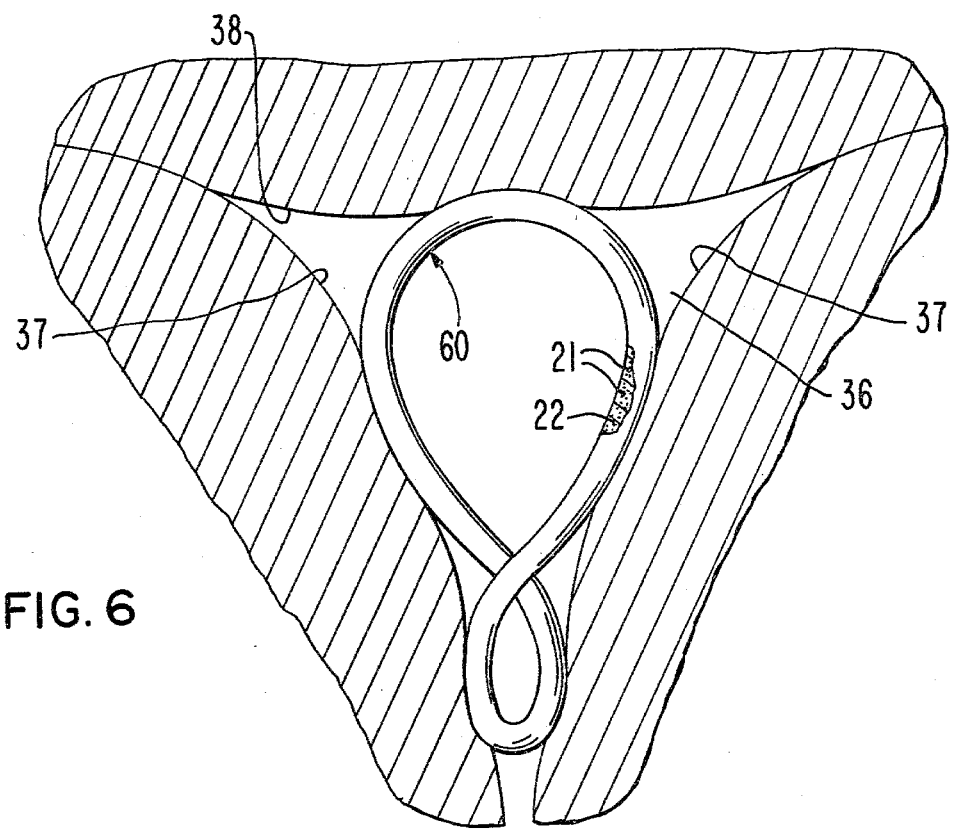
Figure 7:
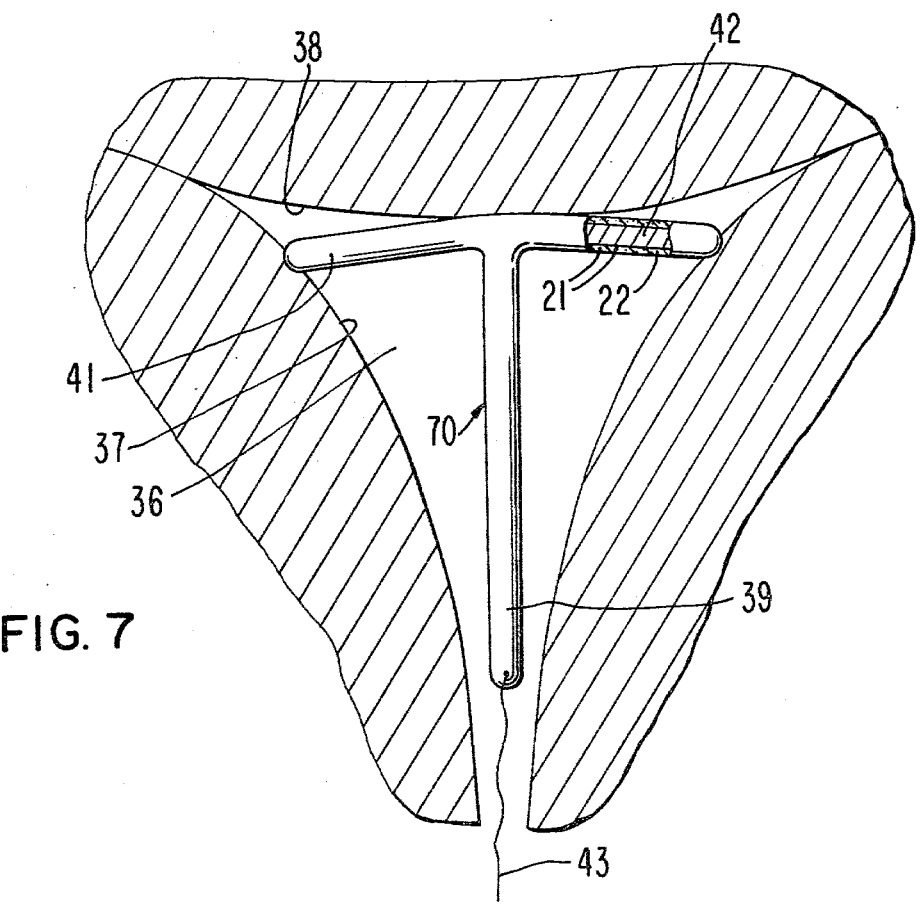

FIGS. 5, 6 and 7 relate to embodiments of this invention adapted for delivering drugs to a mammalian patient. FIG. 5 illustrates as 50 a suppository suitable for rectal or vaginal use.

Suppository 50 is rounded at its top end to permit simple, non-painful insertion. Suppository 50 comprises drug 21 dispersed through poly(carboxylic acid) body 22. When placed in the constant pH vagina or rectum, device 50 erodes and releases drug at a controlled rate over a prolonged period of time.

In FIG. 6 there is depicted an intrauterine drug delivery device 60 embodying the invention. Drug delivery device 60 comprises a body of poly(carboxylic acid) 22 having particles of drug 21 dispersed therethrough. Device 60 consists of two continuous loops each having a crosssectional diameter of about 1.5 to 2.5 cm. The larger of the two loops is adapted to be located within the uterine cavity 36 where it contacts the sides 37 as well as the fundus uteri 38 of the uterus. The smaller loop is positioned in the neck of the uterus to assist in maintaining device 60 within uterine cavity 36. Device 60 slowly erodes in the uterus releasing drug 21 over a prolonged period of time.

FIG. 7 depicts another intrauterine drug delivery device 70 in accord with the invention. This device is in a "T" configuration, having a lateral member or cross bar 41 attached to a depending vertical member or leg 39 and is adapted to be located within a uterine cavity 36, wherein it optionally contacts sides 37 as well as fundus uteri 38. Device 70 is preferably designed with rounded, non-traumatising ends and a thread 43 attached to the trailing end of member 39, distal from the lead or inserting end of the device, for manually removing device 70 from uterus 36. Thread 43 can be any suitable material, for example, nylon surgical thread having a thickness of about 0.002 inches, and the like. Device 70 is shaped and size adapted to be inserted into uterus 36 and be placed and retained there over a prolonged period of time during which drug is delivered. Device 70 is fabricated in another embodiment with a center core 42 optionally not containing drug in the embodiment shown, but is made of a poly(acid), and an outer layer 22 of poly(carboxylic acid) having particles of drug 21 dispersed therethrough. The thickness of layer 22 is small compared to the area of device 70. Device 70 also can be a solid body 22 of erodible poly(acid) which has drug 21 dispersed throughout. As device 70 erodes, it releases entrapped drug 21 and delivers it locally to the uterus in which it is positioned. Drug 21 may be in the form of solid particles, liquid droplets, colloidal particles, or gels, depending upon the nature of the drug. As the device erodes, its surface area decreases. This decrease in area causes the rate of drug release to decrease as well. One way to achieve a more constant rate of drug release is to vary the concentration of drug within the body of erodible poly(acid) 22, increasing the concentration in the inner areas of device 70 so as to compensate for the decrease in area. Thus, the area of erosion does not change substantially during the period of erosion and the rate of erosion remains essentially constant.

Figure 8:
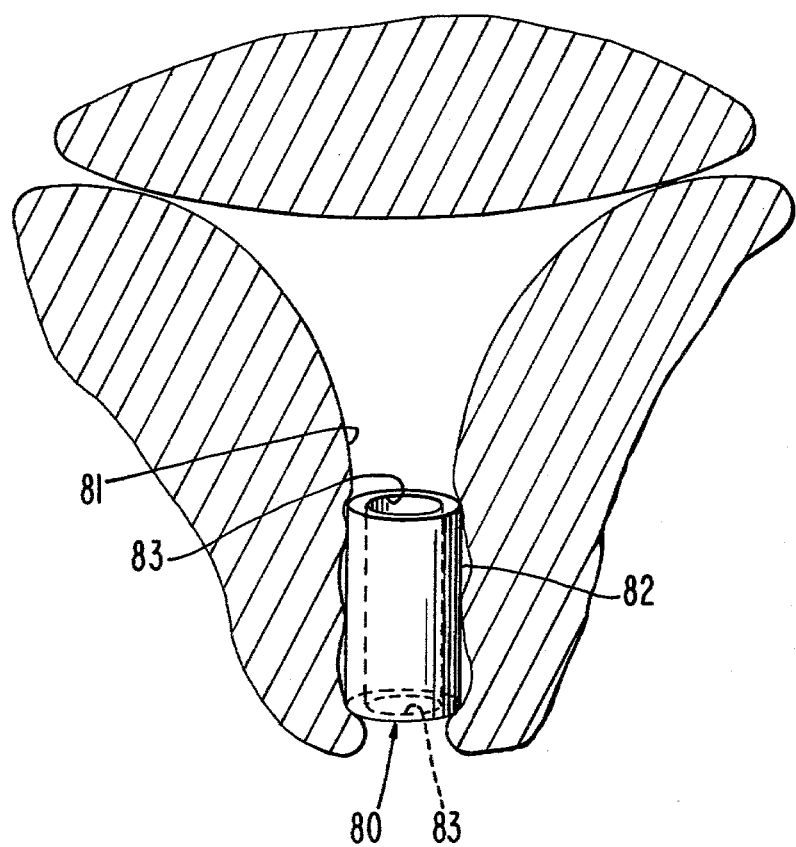
FIG. 8 is a partially sectional elevational view of a device of this invention adapted for placement in the cervical canal of a pregnant female.

FIG. 8 illustrates a device 80 for administering a drug in the cervical canal 81. Device 80 is a hollow, cervical tubular body 82 having a pair of openings 83 and a multiplicity of perforations in its walls, not shown, for the passage of cervical fluid through the device.

The devices of this invention may take on a great variety of sizes and shapes. For example, for application and retention in the human uterus, they generally range in size from about 2 cm to about 6 cm in length and width. For uterine devices for other animals, larger or smaller sizes may be used as required for comfort and uterine retention. The device may take forms such as cylindrical, bullet, elliptical, circular, bulbous, loop, bow, which lend themselves to intrauterine placement or lodging in the cervix uteri. Specific suitable forms include without limitation, Birnberg's Bow shown in U.S. Pat. No. 3,319,625, the Comet shown in U.S. Pat. No. 3,256,878, the Spring of U.S. Pat. No. 3,397,691, Lippes' Loop, the Ring with Tail, the Ota Ring, and the like. The device may also be shaped and size adapted for placement and use in other areas of the mammalian body such as surgical implants and nasal and buccal devices. The embodiments of the devices of this invention are merely illustrative and are not to be construed as limiting the scope of the invention. Other embodiments both for active agent dispensing generally, and drug delivery more specifically, may be employed so long as they are adapted for use in the constant pH environments which this invention requires.

The devices of this invention may be used to deliver controlled flows of any active agent, as the materials have been heretofore described. Preferably, they are employed to deliver drugs. The term "active agent" includes those agents or substances that produce a predetermined beneficial and useful result. The active agents include pesticides, germicides, biocides, algicides, herbicides, rodenticides, fungicides, insecticides, anti-oxidants, plant growth promoters, plant growth inhibitors, preservating agents, surfactants, disinfectants, sterilization agents, catalysts, chemical reactants, fermentation agents, cosmetics, foods, nutrients, food supplements, drugs, vitamins, sex sterilants, fertility inhibitors, fertility promoters, air purifiers, microorganism attenuators, and other like agents that benefit man, animals or the environment.

Devices of this invention are especially useful for delivering all types of drugs. In the specification and accompanying claims, the term "drug" broadly includes physiologically or pharmacologically active substances for producing effects in mammals, including humans, valuable domestic household, sport or farm animals such as horses, dogs, cats, cattle, sheep and the like; or laboratory animals such as mice, monkeys, rats, guinea pigs, and the like. While the devices of this invention operate with special effectiveness with drugs which have a locallized effect, systemically active drugs which act at a point remote from the place of the device, may be administered as well, and they are included within the term "drugs". Thus, drugs that can be administered by the device of the invention include, without limitation: drugs acting on the central nervous system such as, hypnotics and sedatives such as pentobarbital sodium, phenobarbital, secobarbital, thiopental, etc.; heterocyclic hypnotics such as dioxopiperidines, and glutarimides; hypnotics and sedatives such as amides and ureas exemplified by diethylisovaleramide and α-bromoisovaleryl urea and the like; hypnotics and sedative alcohols such as carbomal, naphthoxyethanol, methylparaphenol and the like; psychic energizers such as isocarboxyazid, nialamide, phenelzine, imipramine, tranylcypromine, pargylene, and the like; tranquilizers such as chloropromazine, promazine, fluphenazine, reserpine, deserpidine, meprobamate, benzodiazepines such as chlordiazepoxide and the like; the anticonvulsants primidone, diphenylhydantoin, enitabas, ethotoin, pheneturide, ethosuximide and the like; muscle relaxants and anti-parkinson agents such as mephenesin, methocarbomal, trihexylphenidyl, biperiden, levo-dopa, also known as L-dopa and L-$\beta$-3-4-dihydroxypehnylalanine, and the like; analgesics such as morphine, codeine, meperidine, malorphine, and the like; antipyretics and anti-inflammatory agents such as asprin, salicylamide, sodium salicylamide and the like; local anesthetics such as procaine, lidocaine, naepaine, piperocaine, tetracaine, dibucaine and the like; antispasmodics and anti-ulcer agents such as atropine, scopolamine, methscopolamine oxypenonium, papaverine; antimicrobials such as penicillin, tetracycline, oxytetracycline, chlorotetracycline, chlorampehnicol, sulfonamides and the like; anti-malarials such as 4-aminoquinolines, 8-aminoquinolines and pyrimethamine; hormonal agents such as prednisolone, cortisone, cortisol and triamcinolone; sympathomimetic drugs such as epinephrine, amphetamine, ephedrine, norephineprine and the like; cardiovascular drugs, for example, procainamide, amyl nitrate, nitroglycerin, dipyridamole, sodium nitrate, mannitol nitrate and the like; diuretics, for example, chlorothiazide, flumethiazide and the like; antiparasitic agents such as bephenium hydroxynaphthoate and dichloropehn, dapsone and the like; neoplastic agents such as mechlorethamine, uracil mustard, 5-fluorouracil, 6-thioguanine, procarbazine and the like; hypoglycemic drugs such as insulins, protamine zinc insulin suspension, globin zinc insulin, isophane insulin suspension, and other art known extended insulin suspensions, sulfonylureas such as tolbutamide, acetohexamide, tolazamide, and chlorpropamide, and biguanides and the like; nutritional agents such as enitabas, vitamins, essential amino acids, essential fats and the like; and other physiologically or pharmacologically active agents.

The devices of this invention deliver with special efficiency progestational substances that have antifertility properties and estrogenic substances that have antifertility properties. These substances can be of natural or synthetic origin. They generally possess a cyclopentanophenanthrene nucleous. The term "progestational substance" as used herein embraces "progestogen" which term is used in the pharmaceutically acceptable steroid art to generically describe steroids possessing progestational activity, and the former also includes "progestins", a term widely used for synthetic steroids that have progestational effects. The active antifertility progestational agents that can be used to produce the desired effects in mammals, including humans, include without limitation: pregn-4-ene-3,20-dione, also known as progesterone; 19-nor-pregn-4-en-3,20-dione; 17-hydroxy-19-nor-17α-pregn-5(10)-3-en-20-yn-3one; dl-11β-ethyl-17α-ethynyl-17β-hydroxypregn-4-en-3-one; 17α-ethynyl-17-hydroxy-5(10)-estren-3-one; 17α-ethynyl-19-norestosterone; 6-chloro-17-hydroxypregn-4,6-diene-3,20-dione; 17β-hydroxy-6α-methyl-17-(1-propynyl)androst-4-en-3-one; 9β,10α-pregna-4,6-diene-3,20-dione; 17-hydroxy-17α-pregn-4-en-20-yn-3-one; 19-nor-17α-pregn-4-en-20-yne-3β,17-dial; 17-hydroxy-pregn-4-en-3,20-dione; 17α-hydroxy-progesterone; 17-hydroxy-6α-methyl-pregn-4-ene-3,10-dione; mixtures thereof and the like.

The estrogenic antifertility agents useful herein also include the compounds known as estrogens and the metabolic products thereof that possess antifertility properties or that are converted to active antifertility agents in the uterine environment. Exemplary estrogenic compounds include β-estradiol, β-estradiol 3-benzoate; 17-62 -cyclopentane-propionate estradiol; 1,3,5(10)-estratriene-3,17β-diol dipropionate; estra-1,3,5(10)-triene-3,17-β-diol valerate; estrone; ethinyl estradiol; 17-ethinyl estradiol-3 methyl ether; 17-ethinyl estradiol-3-cyclopento-ether; estriol; mixtures thereof and the like.

Another group of drugs which may be delivered with high efficiency by the devices of this invention include drugs for inducing uterine contractions such as the oxytocic agents, for example, oxytocin, ergot alkaloids such as ergonovine and methylergonomine, quinine, quinidine, histamine and sparteine.

Yet another group of drugs preferred for delivery from the devices of this invention are the prostaglandins. Prostaglandins have a wide range of biological activities. Prostaglandins occur as natural body humoral agents are produced synthetically. Such compounds contain an oxygenated cyclopentane nucleus to which two side chains are attached in the vicinal positions. The hypothetical completely saturated and unsubstituted parent compound of the prostaglandins is called prostanoic acid and is represented by the structural formula:

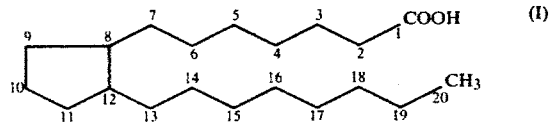

Nomenclature of the prostaglandins is derived from the above formula and numbering system. Therefore, the structure of the prostaglandin nucleus and side chains can be described according to the structure of prostanoic acid shown in Formula I. It has been found that four types of prostaglandin nuclei are present in prostaglandins, which gives rise to four series of prostaglandins commonly designated as E, F, A, and B, which are shown in Formulas II-IV inclusive. In structural formulae II-V, a dotted line represents a valency bond in the α-configuration and the solid line represents a bond in the β-configuration.

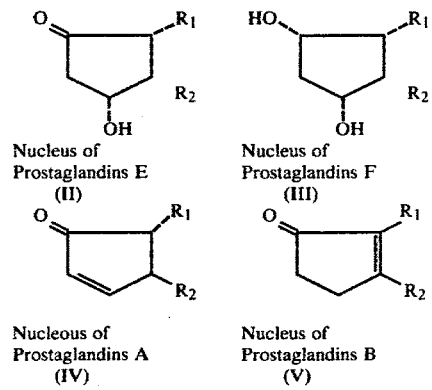

Nucleus of Prostaglandins E (II)

Nucleus of Prostaglandins F (III)

Nucleous of Prostaglandins A (IV)

Nucleus of Prostaglandins B (V)

Among naturally occurring prostaglandins, two side chains have been described. One contains a terminal carboxylic acid group and may also contain a double bond, while the other contains a hydroxyl functional group together with one or two double bonds. These side chains are present in natural prostaglandins in three combinations designated 1, 2, and 3, depending upon the total number of double bonds present, so that the natural prostaglandins are designated as $E_1$, $E_2$, $E_3$, $F_1$, $F_2$, etc. These specific side chains are as follows:

| Prostaglandins | $R_1$ | $R_2$ |
|---|---|---|
| $E_1 F_1 A_1 B_1$ | —$(CH_2)_6$—COOH | —CH:CHCH(OH)$(CH_2)_4$CH$_3$ |
| $E_2 F_2 A_2 B_2$ | —$CH_2CH$:CH$(CH_2)_3$COOH | —CH:CHCH(OH)$(CH_2)_4$CH$_3$ |
| $E_3 F_3 A_3 B_3$ | —$CH_2CH$:CH$(CH_2)_3$COOH | —CH:CHCH(OH)$CH_2$CH:CHCH$_2$ |

In addition to the foregoing natural compounds, various biologically active substituted prostaglandins and prostaglandin analogues are known to the art. These include 19-hydroxy prostaglandins, acyl prostaglandins, alkoxy prostaglandins, esters or amides of the carboxyl group in $R_1$, as well as prostaglandins having alkyl substituents on the $R_1$ and $R_2$ side chains.

While any of the natural and synthetic prostaglandins may be delivered by the present devices, those of A, E, and F nuclei which have been shown to be most useful for producing uterine contractions comprise a preferred group for use in these devices, a group herein defined to be the uterine contraction-inducing prostaglandins. A more preferred group of prostaglandins comprises those of $E_1$, $E_2$, $F_1$, or $F_2$ configurations, with from 0 to 2 additional alkyl substituents (preferably methyl substituents) on chains $R_1$ and $R_2$. A most preferred group of prostaglandins consists of prostaglandin $E_1$ (11α,15(S)-dihydroxy-9-oxo-13-trans-prostenoic acid); prostaglandin $E_2$ (11α,15(S)-dihydroxy-9-oxo-5-cis-13-transprostadienoic acid); prostaglandin $F_{2α}$ (9α,11α,15(S)-trihydroxy-5-cis-13-trans-prostatrienoic acid); and the 15-methyl derivative of prostaglandin $F_{2α}$. Mixtures of the various prostaglandins, either alone or with added hormonal agents, oxytocin, polypeptides and the like, may be used as well.

The pharmaceutically acceptable, non-toxic salts of the prostaglandins can also be used including the non-toxic alkali metal and alkaline earth metal bases such as sodium, potassium, calcium, lithium, copper, and magnesium hydroxides and carbonates and the ammonium salts and substituted ammonium salts, for example, the non-toxic salts of trialkylamides such as triethylamine, trimethylamine, trisopropylamine, procaine, dibenzylamine, triethanolamine N-benzyl-beta-phenylethylamine, ethyldimethylamine, benzylamine, N-(lower) alkylpiperdine, N-ethylpiperidine, 2-methylpiperidine and other physiologically acceptable amines and bases.

The above-described prostaglandins are known to the prior art and they are amply described in references such as *Pharmacological Reviews*, Vol. 20, pages 1 to 48, 1968; *Progress In The Chemistry Of Fats And Other Lipids*, Vol. IX, pages 231 to 273, 1968; *Science*, Vol. 157, pages 382 to 391; *Angewandte Chemie*, Vol. 4, pages 410 to 416, 1965; *The Journal of Biological Chemistry*, Vol. 238, pages 3555 to 3564, 1963; and other literature references.

Representative of other active agents suitable for use with the devices of this invention include without limitation, insecticides applied to immature insects, namely during the embryo, larvae or pupae stage as effecting metamorphosis and leading ot abnormal development, death or the inability to reproduce. These include aliphatic $\alpha,\beta$-unsaturated esters having a lower alkoxy group which are effective for Hemipteran such as Lygaeidae, Miridae and Pyrrhocoridae; Lepidopteran such as Pyralidae, Noctuidae and Gelechiidae; Coleopteran such as Tenebrionidae, *Crysomelidae Plenitabas* and Dermestidae; the Dipteran mosquitos and flies; Homopteran such as asphids and other insects. The compounds are delivered at dosage levels on the order of 0.01 micrograms to 25.0 micrograms per insect.

Additional representative agents include cyclopentane insecticides of the formula:

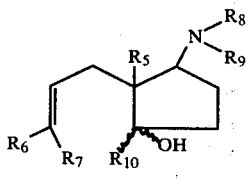

wherein $R_6$, $R_7$, $R_{10}$, $R_8$ and $R_9$ are selected from the group consisting of lower alkyl and $R_5$ is a member selected from the group consisting of methyl and ethyl, for use against Lepidopteran, Diptera, Coleoptera and the like. The device can also be used to deliver juvenile hormones such as methyl-10,11-(cis)osido-7-ethyl-3,11-dimethyltrideca-2(trans), 6(trans)-dienoate and methyl-10,11(cis)oxido-3,7,11-trimethyltrideca-2(trans),6-(trans)-dienoate, and the like.

Other agents which may be delivered by the devices of the invention include herbicides, insecticides, miticides, rodenticides, fungicides and the like, such as 2,3,5-trichloropyridine-4-ol; 4-(methylthio)-3,5-xylyl N-methyl carbamate; O-isopropoxyphenyl N-methyl carbamate; O,O-dimethyl S(N-methylcarbamoyl) methyl phosphorodithioate; 2,4-dichlorophenoxyacetic acid; and the like.

The agent is mixed with the bioerodible material and the mixture is fabricated by casting, and the like, into a form suitable for use in the uterus. The erodible material containing drug may be present as the actual intrauterine device or may as well be present as a pendant, flag, or other suitable attachment auxiliary thereto.

The amount of agent employed in devices in accord with this invention may vary over a wide range, depending upon the type of agent and the delivery rate desired and the size and type of device in which the agent is employed. The amount may vary from the minimum effective single delivery of the agent employed to a maximum amount of agent limited by the size and/or erosion characteristics of the devices. In general, agent is usually present in an amount equivalent to up to about 90% of the weight of the poly(carboxylic acid), although larger or smaller amounts consistant with the above noted general limits may be employed if desired. With the agent loadings of from 0.1 to 40% by weight, based on the poly(carboxylic acid), or 0.1 to 40% by weight per 100% by weight of the polymer are presently used. For drug delivery devices, the amount of drug present in the device is dependent upon the dosage requirement and the length of time the device is to be placed in the biological environment. Thus, a single dose of a very potent drug, which may be as little as a few micrograms, to an amount sufficient for several hundred or even a thousand doses of a less potent drug, such as up to several grams (for example, 5 grams) of drug. In any event, the amount of drug must be small enough that the erodible material is a continuous phase and the drug is a dipersed phase therein. In general, drug too is present in an amount equal to up to about 90% of the weight of bioerodible material. Thus, drug loadings of from about 0.01%, based on the bioerodible material, to about 40% are preferred. That is, for an intrauterine device, 0.01% to 40% by weight per 100% by weight of the polymer per device is presently preferred.

The devices of this invention are intended to release active agent over prolonged periods of time. For example, the devices release drugs locally to the uterus over prolonged periods of time, that is, for periods of from about ¼ hour to 30 days or longer. With the progestational and estrogenic substances, delivery times of from about 1 day to 30 days or 2 years or more are preferred, with dosage rates of from about 5 to 200 mg per day being preferred, thus making it desirable to incorporate at least from about 10 mg to about 6 grams of these substances in a delivery device. When prostaglandins are administered for uterine contraction-inducing purposes, it is preferred to administer the drug over a period of from about 4 hours to about 24 hours at a rate of about 1 microgram/minute to about 25 micrograms/minute. Thus the loading of prostaglandins in the present devices may suitably vary from about 250 micrograms up to as much as about 100 milligrams, depending on the dosage rate and period desired, preferably the loading of prostaglandin would be between about 1 milligram and about 100 milligrams. Similar drug loadings could be determined for the many other dosage periods and amounts. The intrauterine devices gradually erode in the uterus and release their drug. The rate of erosion will depend in part on the recipient's temperature (generally from about 35° C. to 38° C.), uterine pH (generally pH 7-8) and the amount of uterine fluids presently available to contact the device.

The rate of erosion and agent release of materials employed in the invention can be determined experimentally in vitro by testing them under simulated environmental conditions. For example, the rate of erosion of a device in a moving aqueous stream can be determined by placing a device in such a stream and repeatedly weighing it to determine its weight loss. Similarly, the rate of erosion of a material in a biological fluid such as in tear fluids, as would occur with an ocular drug delivery device, amy be measured by placing a small weighed sample of the material in a 0.026 M $HCO_3^-$ solution of pH about 7.4 (simulated tear fluids) at body temperature (37° C.), agitating for a timed interval, and periodically measuring the amount of material eroded into the solution. The rate of erosion of a device in uterine fluids, as would occur with an intrauterine drug delivery device, may be measured by placing a small weighed smaple of the material in physiological saline solution; a solution of pH about 7.4 (simulated uterine fluids) at body temperature (37° C.), agitating for a timed interval, and periodically measuring the amount of material eroded into the solution. To accurately predict in vivo results, it is necessary to multiply the in vitro rates by an experimentally determined constant which takes into account differences in stirring rate and fluid volumes between the living body and the in vitro test apparatus. This constant may be derived in the cast just set forth by first placing a plurality of small weighed samples of material in a plurality of environments such as eyes and uterus, and sequentially over a period of time, removing and weighing the samples. The rate thus determined, divided by the rate of erosion observed in vitro with the same material equals the necessary constant.

For a more complete understanding of the nature of this invention, reference should be made to the following examples which are given merely as further illustrations of the invention, and are not to be construed in a limiting sense. All parts are given by weight, unless stated to the contrary.

DETAILED DESCRIPTION OF EXAMPLES

EXAMPLE 1

A device suitable for releasing drug to the essentially constant pH environment of the eye employing a hydrophobic poly(carboxylic acid) having on an average from 8 to 22 total carbon atoms for each ionizable acidic carboxylic hydrogen and containing hydrocortisone is prepared in the following manner:

A. Preparation of poly(carboxylic acid).

12.6 grams (0.10 equivalents) of ethylene-maleic anhydride copolymer (Monsanto EMA, Grade 31) is stirred with 50 ml (0.4 moles) of n-hexyl alcohol at 120°-125° C. for 7 hours. The solution is cooled to room temperature and methylene chloride is gradually added to the cloud point. Then more methylene chloride is added to precipitate the product (total vol. 3 l). The precipitate is thoroughly leached with the methylene chloride. The solvent is de-canted and the product dissolved in 75 ml warm acetone. Methylene chloride is added to the cloud point. Then more methylene chloride is added to precipitate the product (total vol. 2 l). The precipitate is then thoroughly leached with the methylene chloride. The solvent is decanted and the product dissolved in 75 ml acetone. The solution is transferred to a polypropylene container and solvent is removed under vacuum at 50° C. to yield the polymer product. The infrared spectrum of the polymer shows broad bands at 1680 and 1780 cm$^{-1}$ indicative of ester carboxyl. Titration with base shows that the hexyl half ester of maleic acid has been formed, and thus the ratio of total carbons to ionizable hydrogens on average is 12:1. A sample of the polymer is tested for hydrophobicity by measuring its water absorption and is found to pick up only 6% by weight of water.

B. Preparation of hydrocortisone-containing ocular insert.

1.8 grams of the half ester polymer of part A is dissolved in 5 ml of acetone, with stirring at 25° C. 0.2 grams of micronized hydrocortisone are dispersed in the solution with stirring. The resulting viscous dispersion is drawn on a polyethylene film to a wet thickness of about 0.75 mm. The cast plate is allowed to dry thoroughly to yield a 0.3 mm thick dry film. The resulting film is removed from the polyethylene film by stripping, and is punch cut into desired shapes and sizes. A 6 mm diameter circular disc weighs 7 mg and contains 0.7 mg of hydrocortisone.

C. Testing of inserts.

A series of 0.3 mm thick ocular inserts prepared in part B are each placed in 60 ml portions of simulated tear fluids (water containing 0.1 moles of $K_2HPO_4$ per liter and having a substantially constant pH of 7.4) and agitated at 37° C. for 40 minutes. Sequentially the ocular inserts are retrieved, dried and weighed. The samples of simulated tear fluids are analyzed by ultraviolet absorption at 248 millimicrons wave length for hydrocortisone content. The results of these tests indicate that the inserts erode in this solution of simulated tear fluids in 40 minutes at a uniform rate and that the drug release parallels the erosion. The erosion rate in vitro could be decreased almost 2 orders of magnitude by decreasing the buffer concentration and the rate of stirring. The most reproducible results are obtained at the buffer concentration and rapid stirring rate employed. FIG. 9 illustrates by a graph, drug release rates observed when several series of these inserts are tested in vitro.

A series of these ocular inserts are placed in rabbits' eyes, where they exhibit a similarly uniform but slower rate of erosion and drug release to that observed in the simulated (in vitro) experiments. About 175+ hours are required for complete erosion. The factor In vivo/In vitro equals 0.01.

During the in vivo tests, the rabbits are carefully watched for evidence of ocular irritation. In accordance with the Draize method of measuring ocular irritation, the following conditions are wated for: hyperemia, edema and necrosis of the lids; hyperemia, tearing, chemosis and necrosis of the conjunctiva; exudate from the conjunctiva; follical hypertrophy; and damage to the cornea or iris. Over the period of testing these ocular inserts, at worst, mild irritation is noted.

EXAMPLES 2-6

The ocular insert preparation of Example 1, parts A and B, is repeated 5 times with one variation. The molar excess of n-hexanol employed in Example 1 is replaced with a similar amount of other alkanols as follows:

| Example | Alkanol |
| --- | --- |
| 2 | n-butanol |
| 3 | n-pentanol |
| 4 | n-heptanol |
| 5 | n-octanol |

The ratio of total carbon atoms to ionizable carboxylic hydrogens in each of the resulting half esters is as follows:

| Example | Ratio Carbons Ionizable Hydrogens |
| --- | --- |
| 2 | 10 |
| 3 | 11 |
| 4 | 13 |

-continued

| Example | Ratio Carbons Ionizable Hydrogens |
|---------|-----------------------------------|
| 5 | 15 |
| 6 | 16 |

Water absorption tests show the products to be increasingly hydrophobic, with the product of Example 2 giving the greatest water pickup with the product of Example 6 giving the smallest water pickup.

Erosion tests under the simulated conditions of Part C of Example 1 are carried out. Constant erosion rates and release rates are noted for each of the materials. The results of these tests, as well as the in vivo results which would be predicted for the eye using the factor derived in Part C of Example 1 are as follows:

| Example | Time to Completely Erode In Vitro, Min. | Time to Completely Erode In Vivo, Hrs. |
|---------|------------------------------------------|-----------------------------------------|
| 2 | 10 | 10–15 |
| 3 | 20 | 30 |
| 4 | 50 | 90 |
| 5 | 300 | 550 |
| 6 | 450 | 800–900 |

EXAMPLE 7

A. Preparation of polymer.

A mixture of 5 grams of poly(vinyl methyl ether maleic anhydride) 1:1 molar ratio copolymer (GAF Corp. Gantrez AM 169) and 30 ml of n-pentyl alcohol is stirred at 120° C. for 16 hours to yield a viscous product. This product is poured into 500 ml of 2% $Na_2CO_3$ solution. The resulting solution is extracted twice with 400 ml volumes of hexane and acidified to pH 1–2 with HCl. The precipitated polymer is collected, washed with slightly acidified water and dried. The product is found to be the n-pentyl half ester of maleic acid. The product is hydrophobic, exhibiting an equilibrium water pickup of 9% by weight. It has an average 12 carbon atoms for each ionizable carboxylic hydrogen.

B. Preparation of drug delivery material.

A 5 gram portion of the half ester product of part A is dissolved in 10 grams of acetone with stirring. Micronized progesterone (0.5 grams) is added to the syrupy ethanol solution of ester. The progesterone does not dissolve in the ester solution but forms a uniform suspension. The suspension is cast to a wet thickness of 1.0 mm on silicone release paper. The film is dried in moist air at 25° C. for 72 hours and stripped from the release paper as a cloudy film having a final dry thickness of 0.3 mm. Although the film is somewhat brittle, it is easily punch cut into a variety of shapes suitable for insertion in the uterus.

C. Testing of material.

A 20 mm by 5 mm strip of this film (30 mg) is attached to a Lippes Loop intrauterine device and inserted into the uterus of an adult human female of 40 to 80 hg. wt. The drug delivery material erodes over a period of 30 days releasing about 100 mg of progesterone per day.

EXAMPLE 8

A. Preparation of N-butyl acrylate-methacrylic acid copolymer.

A solution of 288 ml (2.0 mole) of n-butyl acrylate, 85.1 ml (1.0 mole) of methacrylic acid, 0.10 g of benzoyl peroxide, and 1000 ml of ethanol is stirred under nitrogen at 50°–53° C. for 27 hours. The product is isolated by precipitation into petroleum ether and triturated with ethyl ether.

B. Preparation of inserts.

In a stirred flask were mixed the polymer product of part A 20% of sodium dodecyl benzene sulfonate surfactant, 10% of benzalkonium chloride disinfectant and 2% of water soluble green dye. The mixture is cast into 10 gram pellets. When one of these pellets is placed in the water closet of a standard toilet, it releases dye, disinfectant and surfactant to the constant pH water in the water closet over a prolonged period of time, in a manner characterized by being a continuous and prolonged release.

EXAMPLES 9–10

Two 25.2 gram portions of ethylene maleic anhydride copolymer (monsanto EMA, Grade 31) are each dissolved in acetone. To one portion is added 20 grams of water and the mixture is warmed for four hours to yield a fully hydrolyzed ethylene maleic acid copolymer having a total carbon/carboxylic hydrogen ratio of 3. To the other portion is added 7.35 grams of absolute ethanol. The mixture is refluxed for 10 hours. Water (20 mls) is added and the mixture is warmed for 4 hours. Titration analysis indicates that 80% of the original maleic anhydride groups are present in the form of ethyl half esters while the remaining 20% are present as maleic acid. Thus the total carbon/carboxylic hydrogen ratio is about 7. Prior to preparing agent-containing devices of either of these materials, films of the polymers themselves are tested in a simulated constant pH environment. Both prove to be substantially hydrophilic and to erode essentially uncontrollably.

EXAMPLES 11–12

A. Preparation of half esters of N-vinyl pyrrolidone-maleic anhydride copolymers.

A mixture of 11.6 g (0.118 mole) of maleic anhydride (Aldrich Chemical Co.), 12.7 ml (0.121 mole) of N-vinyl pyrrolidone (Aldrich Chemical Co.), 0.12 g azodiisobutyronitrile and 140 ml benzene is stirred under dry nitrogen at 60° C. for 42 hours. The mixture is cooled to room temperature and the product 17.3 g (71%) collected by filtration and characterized as follows:

$\lambda$KBr max 1680, 1780, 1850 $cm^{-1}$; soluble $H_2O$, DMF; insoluble $CH_3OH$ acetone.

The n-hexyl and n-decyl half esters of the poly N-vinyl pyrrolidonemaleic anhydride copolymer are prepared according to the procedure for the preparation of the n-pentyl half ester of (methyl vinyl ether-maleic anhydride) copolymer given in part A of Example 7. Both materials are hydrophobic.

B. Production of devices.

Cortisone acetate (12% basis polymer) is added to the polymer and the mixture formed into a viscous solution in acetone. This solution is cast into a 1.0 mm thick film which is dried, recovered and punch cut into shapes suitable for skin patches.

C. Testing.

The device of part B is tested in the simulated dermal environment. The n-hexyl half ester erodes and releases agent at a constant rate over a 20 minute period. The n-decyl ester device erodes in about 20+ hours.

EXAMPLE 13

A. Preparation of n-butyl acrylate-acrylic acid copolymer.

A solution of 14.4 ml (0.10 mole) of n-butyl acrylate, 6.85 ml (0.10 mole) of acrylic acid, 0.10 g benzoyl peroxide, and 50 ml ethanol is stirred under nitrogen at 48°-52° C. for 40 hours. The product is isolated by precipitation into petroleum ether.

B. Insert production.

In acetone, polymer product of part A and 10% of cortisone are blended. The mixture is cast and formed into devices in accord with the procedures of Example 1, part B.

C. Testing of inserts.

The inserts of part B are tested in the simulated ocular environment test of Example 1, and found to give a uniform rate of erosion and drug release, eroding over a period of 15 minutes.

EXAMPLE 14

A. Preparation of polymer.

100 grams of benzene, 10.4 grams (0.13 mole) of styrene and 10.0 grams (0.10 mole) of maleic anhydride are stirred in the presence of 0.1 grams of bis-azodiisobutyronitrile at 70° C. over night. The mixture is cooled and the product is separated by filtration and washed. Characterization and analysis shows that it is the 1:1 mole ratio copolymer of styrene and maleic anhydride. 10 grams of this polymer is refluxed in ethanol for 10 hours to yield a viscous product. Analysis shows the product to be the ethyl half ester of styrene-maleic acid copolymer, a product which is hydrophobic and has an average of 14 carbon atoms for each ionizable acidic carboxylic hydrogen.

B. Preparation of implant.

10% by weight hydrocortisone implants are prepared by the casting method of Examples 9-14. Acetone is used as solvent for the casting solution. The finished inserts are 0.5 mm thick.

C. Testing of implants.

The implants of part B are tested by the method of Example 1, part C and found to give a linear erosion and drug release.

EXAMPLE 15

A. Preparation of n-butyl acrylate-acrylic acid-methacrylic acid terpolymer.

A solution of 207.1 g (1.617 mole) of n-butyl acrylate, 21.46 g (0.301 mole) acrylic acid, 41.31 g (0.480 mole) methacrylic acid, 1.30 g benzoyl peroxide and 650 ml of ethanol is stirred under nitrogen at 50°-53° C. for 65 hours. The product is isolated by precipitation into 12 liters of hexane and purified by repeated dissolution in approximately 600 ml acetone and precipitation into hexane.

B. Preparation of insert device.

10% by weight brominated salicylanilide devices are prepared by the casting method of Examples 9-14. Ethanol is used as solvent for the casting solution. The finished inserts are 0.5 mm thick.

C. Testing of inserts.

The devices of part B are tested by the method of Example 1, part C and found to give a linear erosion and brominated salicylanilide release.

EXAMPLE 16

A. Preparation of n-pentyl acrylate-n-hexyl methacrylate-acrylic acid terpolymer.

A solution of 116.59 g (0.82 mole) of n-pentyl acrylate, 85.12 g (0.50 mole) n-hexyl methacrylate, 77.82 g (1.08 mole) acrylic acid, 1.30 g benzoyl peroxide and 650 ml of ethanol is stirred under nitrogen at 50°-53° C. for 65 hours. The product is isolated by precipitation into 12 liters of hexane and purified by repeated dissolution in approximately 600 ml acetone and precipitation into hexane.

B. Preparation of insecticide releasing device.

10% by weight ethyl 4,4'-dichlorobenzilate devices are prepared by the casting method of Examples 9-14. Ethanol is used as solvent for the casting solution. The finished devices are 0.5 mm thick.

C. Testing of inserts.

The inserts of part B are testing by the method of Example 1, part C and found to give a linear erosion and ethyl 4,4'-dichlorobenzilate release.

EXAMPLE 17

A. Preparation of a homogenous n-butyl acrylate-acrylic acidmethacrylic acid terpolymer.

The terpolymers prepared as described in Examples 15 and 16 due to the differences in reactivity ratios, are compositionally quite heterogenous. In this example, compositionally homogenous terpolymers can be prepared using the following procedure: butyl acrylate (62.46 g, 0.4875 mole), acrylic acid (7.50 g, 0.104 mole), methacrylic acid (5.80 g, 0.0675 mole), 2,2'-azobis(2-methylpropionitrile) (108 mg), and methanol (425 ml) are placed in a 1 liter 3-neck flask equipped with a condenser, magnetic stirrer, nitrogen line and serum stopper and cooled with an ice bath. The solution and system are deaerated. A dropping funnel containing 210 ml deareated methanol is attached to the condenser. Two 50 cc syringes, colled in a refrigerator, are filled with a deaerated solution composed of the 3 monomers in the molar ratio of 67.5:12.5:20 (butyl acrylate, 64.8 g, 0.505 mole, acrylic acid, 6.75 g, 0.0938 mole and methacrylic acid, 12.9 g, 0.150 mole).

Delivery of the solution is metered by an infusion pump through a 0.045 inch polyethylene tube. A catalyst solution (150 mg of AIBN in 11.8 ml of methanol) is similarly prepared. The reaction mixture is brought to reflux with an oil bath, concommitantly initiating the delivery of monomer solution (0.22 ml/min from each of the two syringes) and the delivery of a catalyst solution (0.077 ml/min). Methanol is added to the refluxing reaction solution in 15 ml increments every 15 minutes. A total of 45 ml of monomer feed and 10 ml of catalyst solution is added durign the 3 hours. The reaction solution is worked up by pouring it into excess water, drying the precipitate, and re-precipitating the product in acetone with hexane.

B. Preparation of herbicide devices.

0.5 to 20% by weight of 2,4-dichlorophenoxyacetic acid are prepared by the casting procedure described above. The finished filled device is 0.75 mm thick, and was cut into 1 cm squares. These were placed in a hollow, perforated container for linear erosion and release of herbicide.

EXAMPLES 18-20

To three 10 gram portions of the n-butyl half ester material of Example 2 is added respectively 1 g of 1,2-dihydro-pyridazine-3,6-dione; 0.2 g of 2-chloro-4,6-bis-(ethylamino)-1,3,5-triazine; and 0.4 g of a metabolite of Gibberella fijikuroi. Each of these is shaped into an elongated device made with the erodible hexyl half ester of Example 1, and dipped into these solutions and dried. 100 mg of material is deposited. Some devices are dipped into the second and third solutions. Other deposits, such as 500 mg or more can alos be deposited. The devices release insecticide for about 24 hours, with linear erosion concommitantly with insecticide release.

EXAMPLE 21

A device suitable for releasing drug to the uterus employing a hydrophobic poly(carboxylic acid) having on an average from 8 to 22 total carbon atoms for each ionizable acidic carboxylic hydrogen and containing β-estradiol is prepared by using the poly(carboyxlic acid) prepared in Example 1. The β-estradiol is added to the intrauterine device as follows:

1.8 g of the half ester polymer of part A is dissolved in 5 ml of acetone, with stirring at 25° C. 0.2 g of crystalline β-estradiol are dispersed in the solution with stirring. The resulting viscous dispersion is drawn on an inert surface to a wet thickness of about 0.75 mm. The cast plate is allowed to dry thoroughly to yield a 0.3 mm thick dry film. The resulting film is removed from the surface by stripping. A 6 mm×10 mm strip weighs 15 mg and contains 1.5 mg of β-estradiol. The device was then tested in the following manner:

A 6 mm×10 mm strip of the material is placed in a 60 ml portion of simulated uterine fluid (physiological saline solution having a pH of 7.3) and agitated at 37° C. for 40 minutes. Periodically, during the agitation the strip is removed, dried and weighed. At the same time, the β-estradiol content of the simulated uterine fluid is determined by measuring the infrared absorption at 225 and 280 millimicrons and comparing the absorption to a previously prepared concentration/absorption correlation.

This test shows the uterine device erodes at an essentially constant rate over a period of 40 minutes. Drug release is proportional to erosion. A second device is bonded to an opened ring-shaped intrauterine device and inserted in a human uterus. There is erodes over a period of 200 hours; the slower erosion being a function of the rate of stirring and the like, releasing β-estradiol locally to the uterus throughout this prolonged period. The ratio of In Vitro Rate/In Vivo Rate in this test is observed to be about 300.

EXAMPLES 22-26

The preparation set forth in Example 21 is repeated 5 times with one variation. The molar excess of n-hexanol employed in Example 21 is replaced with a similar amount of other alkanols as follows:

| Example | Alkanol |
| --- | --- |
| 22 | n-butanol |
| 23 | n-pentanol |
| 24 | n-heptanol |
| 25 | n-octanol |

The ratio of total carbon atoms to ionizable carboxylic hydrogens in each of the resulting half esters is as follows:

| Example | Ratio Carbons Ionizable Hydrogens |
| --- | --- |
| 22 | 10 |
| 23 | 11 |
| 24 | 13 |
| 25 | 15 |
| 26 | 16 |

Water absorption tests show the products to be increasingly hydrophobic, with the product of Example 22 giving the greatest water pick up with the product of Example 26 giving the smallest water pick up. Erosion tests under the simulated conditions, and release rates, are noted for each of the materials. The results of these tests, as well as the in vivo uterine results which would be predicted are as follows:

| Example | Time to Completely Erode In Vitro, Min. | Time to Completely Erode In Uterus, Hrs. |
| --- | --- | --- |
| 22 | 10 | 30-40 |
| 23 | 20 | 90 |
| 24 | 50 | 270 |
| 25 | 300 | 1600 |
| 26 | 450 | 2000-2500 |

EXAMPLE 27

A. Preparation of polymer

A mixture of 5 g of poly(methyl vinyl ether maleic anhydride) 1:1 molar ratio copolymer (GAF Corp. Gantrez An 169) and 30 ml of n-pentyl alcohol is stirred at 120° C. for 16 hours to yield a viscous product. This product is poured into 500 ml of 2% $Na_2CO_3$ solution. The resulting solution is extracted twice with 400 ml volumes of hexane and acidified to pH 1-2 with HCl. The precipitated polymer is collected, washed with slightly acidified water and dried. The product is found to be the n-pentyl half ester of the maleic acid methyl vinyl ether copolymer. The product is hydrophobic, exhibiting an equilibrium water pick up of 9% by weight. It has an average 12 carbon atoms for each ionizable carboxylic hydrogen.

B. Preparation of uterine delivery material

A 5 g portion of the half ester is dissolved in 10 g of acetone with stirring. Micronized progesterone (0.5 grams) and 2 g of decanol plasticizer are added to the syrupy ethanol solution of ester. The progesterone does not dissolve in the ester solution but forms a uniform suspension. The suspension is cast to a wet thickness of 0.1 mm on silicone release paper. The film is dried in moist air at 25° C. for 72 hours and stripped from the release paper as a cloudy film having a final dry thickness of 0.3 mm. Although the film is somewhat brittle, it is easily punch cut into a variety of shapes suitable for insertion in the uterus.

C. Assay of material

A 20 mm×5 mm strip of this film (30 mg) is attached to a "T" shaped intrauterine device of a size of aobut 2 cm across its top bar and about 3 cm along its center bar, and inserted into the uterus of an adult human female. The drug delivery material erodes over a period of 30 days releasing about 100 micrograms of progesterone per day.

EXAMPLES 28-30

To three 10 gram portions of the n-butanol half ester material of Example 22 are added respectively: 1.0 g of the prostaglandin commonly known as $PGF_{2\alpha}$, 0.2 g of the prostaglandin known at $PGE_2$, and 0.4 g of $PGE_2$. Each of these mixtures is dissolved in acetone. A multi-armed "T" shaped intrauterine device, made with a bioerodible flexible center bar and cross arms of the erodible hexyl half ester of Example 21, has the lower end of its center bar repeatedly dipped into the first of these solutions and dried. 100 mg of ester and prostaglandin is deposited. Second and third multi-armed "T" devices are dipped into the second and third solution. 100 mg each of these polymer and prostaglandin mixtures are deposited. It would be possible, of course, to deposit more, say 500 mg, or less, say 60 mg, of the mixtures.

The three devices are gently inserted into uteri of three first trimester pregnant women. The devices release respectively: 10 micrograms/minute of PGF$_{2\alpha}$, 2 micrograms/minutes of PGE$_2$, and 4 micrograms/minute of PGE$_2$, all for periods of about 24 hours. After another 24 to 48 hours, the erodible cross arms begin to drop off and the devices are expelled. These releases of prostaglandins are sufficient to cause uterine contractions and are suitable for effecting therapeutic abortion. Varying the concentration of prostaglandin from about 1% to about 20% basis polymer would give delivery rates of from about 1 $\mu$g/minute to about 20 $\mu$g/minute.

EXAMPLE 31

An intrauterine device shaped like a triangle is prepared from half estes of N-vinyl pyrrolidone maleic anhydride copolymers. A mixture of 11.6 g (0.118 mole) of maleic anhydride (Aldrich Chemical Co.), 12.7 ml (0.121 mole) of N-vinyl pyrrolidone (Aldrich Chemical Co.), 0.12 g azodiisobutyronitrile and 140 ml benzene is stirred under dry nitrogen at 60° C. for 42 hours. The mixture is cooled to room temperature and the product 17.3 g (71%) collected by filtration and characterized as follows:

$\lambda$ KBr max 1680, 1780 cm$^{-1}$; soluble H$_2$O, DMF; insoluble CH$_3$OH, acetone. The n-hexyl and n-decyl half esters of the poly N-vinyl pyrrolidone maleic anhydride copolymer are prepared according to the procedure for the preparation of the n-pentyl half ester of (methyl vinyl ether-maleic anhydride) copolymer as previously described. Next, progesterone, 8% based on the weight of the polymer, is added to the polymer, the mixture formed into a viscous solution in acetone, and cast into a 1.0 mm thick triangle which is dried and used as an intrauterine device.

EXAMPLE 32

Preparation of a vaginal device

A solution of 14.4 ml (0.10 mole) of n-butyl acrylate, 6.85 ml (0.10 mole) of acrylic acid, 0.10 g benzoyl peroxide, and 50 ml ethanol is stirred under nitrogen at 48° to 52° C. for 40 hours. The product is isolated by precipitation into petroleum ether. Next, the polymer and progesterone are blended, cast into an open ring mold shaped and adapted for vaginal placement, and dried. The device gives a uniform rate of erosion and simultaneously releases progesterone as erosion occurs.

EXAMPLE 33

An interauterine device made of a terpolymer of n-butyl acrylate-acrylic acid-methacrylic acid is prepared as follows: A solution of 207.1 g (1.617 mole) of n-butyl acrylate, 21.46 g (0.301 mole) acrylic acid, 41.31 g (0.480 mole) methacrylic acid, 1.30 g benzoyl peroxide and 650 ml of ethanol is stirred under nitrogen at 50° to 53° C. for 65 hours. The product is isolated by precipitation into 12 liters of hexane and purified by repeated dissolution in approximately 600 ml acetone and precipitation into hexane. Next, 22% by weight of oxytocin is added and the mixture cast as previously described into uterine devices 25 mm long and 0.5 mm thick. The devices have a linear erosion and linear release of drug.

EXAMPLE 34

Precipitation of intrauterine drug releasing device made of n-pentyl acrylate-n-hexyl methacrylate-acrylic acid terpolymer. First, a solution of 116.59 g (0.82 mole) of n-pentyl acrylate, 85.12 g (0.50 mole) n-hexyl methacrylate, 77.82 g (1.08 mole) acrylic acid, 1.30 g benzoyl peroxide and 650 ml of ethanol is stirred under nitrogen at 50° to 53° C. to 65 hours. The product is isolated by precipitation into 12 liters of hexane and purified by repeated dissolution in approximately 600 ml acetone and precipitation into hexane. The polymer is charged with pregn-4-ene-3,20-dione and molded into oval shaped strip for insertion into the uterus. The device gives a linear erosion and steroid release.

EXAMPLE 35

In this example, an intrauterine device is made from a compositionally homogeneous terpolymer prepared by using the following procedure: butyl acrylate (62.46 g, 0.4875 mole), acrylic acid (7.50 g, 0.104 mole), methacrylic acid (5.80 g, 0.0675 mole), 2,2'-azobic [2-methylpropionitrile] (108 mg), and methanol (425 ml) are placed in a 1 liter 3-neck flask equipped with a condenser, magnetic stirrer, nitrogen line and serum stopper and cooled with an ice bath. The solution and system are deareated. A dropping funnel containing 210 ml deaerated methanol is attached to the condenser. Two 50 cc syringes, cooled in a refrigerator, are filled with a deaerated solution composed of the 3 monomers in the molar ratio of 67.5:12.5:20 (butyl acrylate 64.8 g, 0.505 mole, acrylic acid 6.75 g, 0.0938 mole and methacrylic acid, 12.9 g, 0.150 mole).

Delivery of the solution is metered by an infusion pump through a 0.045 inch polyethylene tube. A catalyst solution (150 mg of AIBN in 11.8 ml of methanol) is similarly prepared. The reaction mixture is brought to reflux with an oil bath, concommitantly initiating the delivery of monomer solution (0.22 ml/min from each of the two syringes) and the delivery of a catalyst solution (0.77 ml/min). Methanol is added to the refluxing reaction solution in 15 ml increments every 15 min. A total of 45 ml of monomer feed and 10 ml of catalyst solution is added during the 3 hours. The reaction solution is worked by pouring it into excess water, drying the precipitate and re-precipitating the product in acetone with hexane. To a section of the polymer is added 0.5 to 20% by weight of a mixture of estrone and progesterone and molded into intrauterine shaped devices. The device made of the terpolymer is a means for releasing the drug by linear bioerosion at a uterine pH when placed in situ.

EXAMPLES 36-45

Repeating the procedures of Examples 1 through 35, agent delivery devices, sized shaped and adapted for insertion and placement for administering drug to a mammalian drug receptor site, with the devices having a means for releasing agent concomitantly with the bioerosion of the device at mammalian pH are made as described. The devices have a configuration and means for maintaining in the corresponding body area and they are a member selected from the group consisting of a nasal delivery device, an anal delivery device, an ear delivery device, a vaginal delivery device, a topical delivery device, an implant delivery device, a device for positioning in a non-reproductive body cavity, and a device for delivering to non-biological environments, and the like. These devices have a wall that is a reservoir for containing the agent and a means for its delivery to the receptor site.

The above examples and disclosures are set forth merely for illustrating the mode and the manner of the invention as various modifications and embodiments can be made by those skilled in the art, in the light of the invention without department from the spirit of the invention.

What is claimed is:

1. A surgical implant for the controlled and continuous administration of an active drug to an implant receiving animal having an essentially constant pH throughout the period of administration, the implant consisting essentially of a body sized, shaped and adapted for placement and retention in the animal, said body formed of a bioerodible drug release rate controlling material containing the active drug, the material comprising a hydrophobic poly(carboxylic acid) having one ionizable carboxylic hydrogen atom for each 8 to 22 carbon atoms, which material bioerodes at a controlled and continuous rate over a prolonged period of time in response to the essentially constant pH in the range of from pH 6 to pH 9, by a process of carboxylic hydrogen ionization, thereby releasing the active drug at a controlled and continuous rate to the animal over a prolonged period of time.

2. The surgical implant for the controlled and continuous administration of the active drug to the animal according to claim 1 wherein the body is a matrix and the drug is dispersed therethrough.

3. The surgical implant for the controlled and continuous administration of the active drug to the animal according to claim 1 wherein the body is a hollow reservoir and the drug is in the reservoir.

4. The surgical implant for the controlled and continuous administration of the active drug to the animal according to claim 1 wherein the implant is implanted subcutaneously in the animal.

5. A suppository for the controlled and continuous administration of an active drug to the rectal environment having essentially constant pH throughout the period of rectal administration, said suppository consisting essentially of a body, sized and shaped for placement in the rectal environment, said body formed of a bioerodible drug release rate controlling material containing the active drug, the material comprising a hydrophobic poly(carboxylic acid) having one ionizable carboxylic hydrogen atom for each 8 to 22 carbon atoms, which material bioerodes at a controlled and continuous rate over a prolonged period of time in response to the essentially constant pH environment in the range from pH 6 to pH 9, by a process of carboxylic hydrogen ionization, thereby releasing the active drug at a controlled and continuous rate to the rectal environment over a prolonged period of time.

6. The suppository for the controlled and the continuous administration of the active drug to the rectal environment according to claim 5 wherein the body is a matrix and the drug is dispersed therethrough.

7. The suppository for the controlled and the continuous administration of the active drug to the rectal environment according to claim 5 wherein the body is a hollow reservoir and the drug is in the reservoir.

8. A bioerodible device for the controlled and continuous topical administration of an active drug to an animal having an essentially constant pH throughout the period of drug administration, said device consisting essentially of a body shaped and adapted for topical placement and retention on the animal and formed of a bioerodible drug release rate controlling material containing the active drug, the material comprising a hydrophobic poly(carboxylic acid) having one ionizable hydrogen for each 8 to 22 carbon atoms, which material bioerodes at a controlled and continuous rate over a prolonged period of time in response to the essentially constant pH environment in the range of from pH 6 to 9, by a process of carboxylic hydrogen ionization, thereby releasing the active drug at a controlled and continuous rate to the animal over a prolonged period of time.

9. The bioerodible device for the controlled and continuous topical administration of drug to the animal according to claim 8 wherein the topical placement consists in nasal administration of the drug.

10. The bioerodible device for the controlled and continuous topical administration of drug to the animal according to claim 8 wherein the topical placement consists in buccal administration of the drug.

11. The bioerodible device for the controlled and continuous topical administration of drug to the animal according to claim 8 wherein the body is a matrix and the drug is dispersed therethrough.

12. The bioerodible device for the controlled and continuous administration of drug to the animal according to claim 8 wherein the body is a hollow reservoir and the drug is in the reservoir.

13. A bioerodible device for the controlled and continuous administration of an active drug to an animal drug receptor site having an essentially constant pH throughout the period of drug administration, the device comprising a body sized, shaped and structured for administrating drug to the animal receptor and formed of a bioerodible material containing the active drug, said material a terpolymer comprising a monomeric unit consisting of at least one $\alpha,\beta$-unsaturated aliphatic acid of 3 to 8 carbon atoms, a monomeric unit consisting of an alkyl ester of an $\alpha,\beta$-unsaturated aliphatic acid in which said alkyl group is of 2 to 8 carbon atoms, and a monomeric unit selected from acrylic acid and lower substituted acrylic acids of 4 to 8 carbon atoms, which terpolymer bioerodes at a controlled and continuous rate over a prolonged period of time in response to the essentially constant pH in the range of from pH 6 to pH 9, by a process of carboxylic hydrogen ionization, thereby releasing the active drug from the bioeroding terpolymer at a controlled and continuous rate to the animal receptor over a prolonged period of time.

14. The bioerodible device for the controlled and continuous administration of the active drug to the animal drug receptor site according to claim 13 wherein the body is a matrix and the drug is in the matrix.

15. The bioerodible device for the controlled and continuous administration of the active drug to the animal drug receptor site according to claim 13 wherein the body is a hollow reservoir and the drug is in the reservoir.

* * * * *